(12) United States Patent
Genin et al.

(10) Patent No.: US 12,220,303 B1
(45) Date of Patent: Feb. 11, 2025

(54) ARTICLE FOR ABSORBING BODILY DISCHARGES OF A USER

(71) Applicants: Andrei Genin, Hawthorne, CA (US); Sairhey Ulasevich, Hawthorne, CA (US); Ruslana Kysil, Zhovkva (UA)

(72) Inventors: Andrei Genin, Hawthorne, CA (US); Sairhey Ulasevich, Hawthorne, CA (US); Ruslana Kysil, Zhovkva (UA)

(73) Assignees: Andrei Genin, Miami, FL (US); Sairhey Ulasevich, Miami, FL (US); Ruslana Kysil, Miami, FL (US)

(*) Notice: Subject to any disclaimer, the term of this patent is extended or adjusted under 35 U.S.C. 154(b) by 0 days.

(21) Appl. No.: 18/744,972

(22) Filed: Jun. 17, 2024

(51) Int. Cl.
A61F 13/47 (2006.01)
A61F 13/472 (2006.01)

(52) U.S. Cl.
CPC .... *A61F 13/4702* (2013.01); *A61F 13/47218* (2013.01); *A61F 13/47272* (2013.01)

(58) Field of Classification Search
CPC .............. A61F 13/2011; A61F 13/4702; A61F 13/47218; A61F 13/47272; A61F 13/4758; A61F 2013/1513; A61F 2013/4706; A61F 2013/4729; A61F 2013/47209
See application file for complete search history.

(56) References Cited

U.S. PATENT DOCUMENTS

| 3,183,909 | A | * | 5/1965 | Roehr | A61F 13/47227 604/377 |
| 8,870,842 | B2 | * | 10/2014 | Hill | A61F 13/47227 604/385.17 |
| 9,757,281 | B2 | * | 9/2017 | Goldsmith | A61F 13/47218 |
| 10,307,307 | B2 | * | 6/2019 | Pintado | A61F 13/47227 |
| D1,026,220 | S | | 5/2024 | Kysil et al. | |
| 2008/0172018 | A1 | | 7/2008 | Chien | |
| 2009/0088716 | A1 | * | 4/2009 | Nwokeji | A61F 13/47272 604/386 |
| 2012/0059344 | A1 | | 3/2012 | Seo | |
| 2015/0173969 | A1 | | 6/2015 | Goldsmith et al. | |
| 2016/0228304 | A1 | | 8/2016 | Orechva | |

(Continued)

FOREIGN PATENT DOCUMENTS

| CN | 1426768 A | 7/2003 |
| CN | 200957136 Y | 10/2007 |
| CN | 100548251 C | 10/2009 |

(Continued)

*Primary Examiner* — Catharine L Anderson
(74) *Attorney, Agent, or Firm* — Nitin Kaushik

(57) ABSTRACT

An article for absorbing bodily discharges of a user includes an absorbent element. Further, the absorbent element is configured to be disposed in an intergluteal cleft of the user. Further, the absorbent element includes a base portion, a first portion, and a second portion. Further, the first portion is attached to the base portion on a first side of the base portion and the second portion is attached to the base portion on a second side of the base portion. Further, the first side opposes the second side. Each of the first portion and the second portion extends vertically away from the base portion. Further, the absorbent element includes an outer layer and an inner layer. Further, the inner layer is disposed below the outer layer. Further, the outer layer collects a bodily discharge of the user and the inner layer absorbs the bodily discharge collected by the outer layer.

19 Claims, 25 Drawing Sheets

(56) References Cited

U.S. PATENT DOCUMENTS

2022/0241120 A1   8/2022   Praag

FOREIGN PATENT DOCUMENTS

| | | |
|---|---|---|
| CN | 104107114 A | 10/2014 |
| CN | 104758123 A | 7/2015 |
| CN | 204501251 U | 7/2015 |
| CN | 204600909 U | 9/2015 |
| CN | 110461289 A | 11/2019 |
| CN | 110709044 A | 1/2020 |
| CN | 113301875 A | 8/2021 |
| CN | 214761819 U | 11/2021 |
| DE | 19904482 A1 | 8/2000 |
| EP | 0249405 A2 | 12/1987 |
| ES | 1074277 U | 4/2011 |
| FR | 2915370 A1 | 10/2008 |
| JP | H0563527 U | 8/1993 |
| KR | 20070107032 A | 11/2007 |
| WO | 2011131020 A1 | 10/2011 |
| WO | 2012092783 A1 | 7/2012 |
| WO | 2013101266 A1 | 7/2013 |
| WO | 2021116506 A1 | 6/2021 |

\* cited by examiner

ARTICLE FOR ABSORBING BODILY DISCHARGES OF A USER

FIELD OF THE INVENTION

Generally, the present disclosure relates to the field of apparel. More specifically, the present disclosure relates to an article for absorbing bodily discharges of a user.

BACKGROUND OF THE INVENTION

Existing sanitary napkins are too long and thick, and do not cope well with the problem of night leaks. Further, the existing sanitary napkins also do not prevent leaking of bodily discharges when a person is lying down. Further, the bodily discharge still flows along the existing sanitary napkin beyond the existing sanitary napkin's limits and stains underwear and bed linen when the person wearing the existing sanitary napkin lies down.

Therefore, there is a need for an improved article for absorbing bodily discharges of a user that may overcome one or more of the above-mentioned problems and/or limitations.

SUMMARY OF THE INVENTION

This summary is provided to introduce a selection of concepts in a simplified form, that are further described below in the Detailed Description. This summary is not intended to identify key features or essential features of the claimed subject matter. Nor is this summary intended to be used to limit the claimed subject matter's scope.

Disclosed herein is an article for absorbing bodily discharges of a user, in accordance with some embodiments. Accordingly, the article may include an absorbent element. Further, the absorbent element may be configured to be disposed in an intergluteal cleft of the user. Further, the absorbent element may include a base portion, a first portion, and a second portion. Further, the first portion may be attached to the base portion on a first side of the base portion and the second portion may be attached to the base portion on a second side of the base portion. Further, the first side opposes the second side. Further, each of the first portion and the second portion extends vertically away from the base portion. Further, the absorbent element may include an outer layer and an inner layer. Further, the inner layer may be disposed below the outer layer. Further, the outer layer collects a bodily discharge of the user and the inner layer absorbs the bodily discharge collected by the outer layer.

Further disclosed herein is an article for absorbing bodily discharges of a user, in accordance with some embodiments. Accordingly, the article may include an absorbent element and an absorbent pad. Further, the absorbent element may be configured to be disposed in an intergluteal cleft of the user. Further, the absorbent element may include a base portion, a first portion, and a second portion. Further, the first portion may be attached to the base portion on a first side of the base portion and the second portion may be attached to the base portion on a second side of the base portion. Further, the first side opposes the second side. Further, each of the first portion and the second portion extends vertically away from the base portion. Further, the absorbent element may include an outer layer and an inner layer. Further, the inner layer may be disposed below the outer layer. Further, the outer layer collects a bodily discharge of the user and the inner layer absorbs the bodily discharge collected by the outer layer. Further, the absorbent pad may be configured to be disposed in at least a portion of a crotch region of the user. Further, the absorbent pad may include a top layer, a bottom layer, and at least one absorbent material layer. Further, the top layer opposes at least the portion of the crotch region based on the disposing of the absorbent pad in at least the portion of the crotch region. Further, the bottom layer may be disposed below the top layer. Further, the at least one absorbent material layer may be disposed between the top layer and the bottom layer. Further, the absorbent element may be attached to the absorbent pad. Further, the disposing of the absorbent element in the intergluteal cleft may be based on the disposing of the absorbent pad in at least the portion of the crotch region of the user.

Further disclosed herein is an article for absorbing bodily discharges of a user, in accordance with some embodiments. Accordingly, the article may include an absorbent element and an absorbent pad. Further, the absorbent element may be configured to be disposed in an intergluteal cleft of the user. Further, the absorbent element may include a base portion, a first portion, and a second portion. Further, the first portion may be attached to the base portion on a first side of the base portion and the second portion may be attached to the base portion on a second side of the base portion. Further, the first side opposes the second side. Further, each of the first portion and the second portion extends vertically away from the base portion. Further, the absorbent element may include an outer layer and an inner layer. Further, the inner layer may be disposed below the outer layer. Further, the outer layer collects a bodily discharge of the user and the inner layer absorbs the bodily discharge collected by the outer layer. Further, the absorbent pad may be configured to be disposed in at least a portion of a crotch region of the user. Further, the absorbent pad may include a top layer, a bottom layer, and at least one absorbent material layer. Further, the top layer opposes at least the portion of the crotch region based on the disposing of the absorbent pad in at least the portion of the crotch region. Further, the bottom layer may be disposed below the top layer. Further, the at least one absorbent material layer may be disposed between the top layer and the bottom layer. Further, the absorbent element may be attached to the absorbent pad. Further, the disposing of the absorbent element in the intergluteal cleft may be based on the disposing of the absorbent pad in at least the portion of the crotch region of the user. Further, the absorbent pad may include a front portion and a rear portion. Further, the absorbent element may be attached to the rear portion of the absorbent pad. Further, the absorbent element may be further centrally and longitudinally attached to the rear portion of the absorbent pad.

Both the foregoing summary and the following detailed description provide examples and are explanatory only. Accordingly, the foregoing summary and the following detailed description should not be considered to be restrictive. Further, features or variations may be provided in addition to those set forth herein. For example, embodiments may be directed to various feature combinations and sub-combinations described in the detailed description.

BRIEF DESCRIPTION OF THE DRAWINGS

The accompanying drawings, which are incorporated in and constitute a part of this disclosure, illustrate various embodiments of the present disclosure. The drawings contain representations of various trademarks and copyrights owned by the Applicants. In addition, the drawings may contain other marks owned by third parties and are being used for illustrative purposes only. All rights to various trademarks and copyrights represented herein, except those belonging to their respective owners, are vested in and the property of the applicants. The applicants retain and reserve all rights in their trademarks and copyrights included herein, and grant permission to reproduce the material only in connection with reproduction of the granted patent and for no other purpose.

Furthermore, the drawings may contain text or captions that may explain certain embodiments of the present disclosure. This text is included for illustrative, non-limiting, explanatory purposes of certain embodiments detailed in the present disclosure.

DETAILED DESCRIPTION OF THE INVENTION

Figure 1:
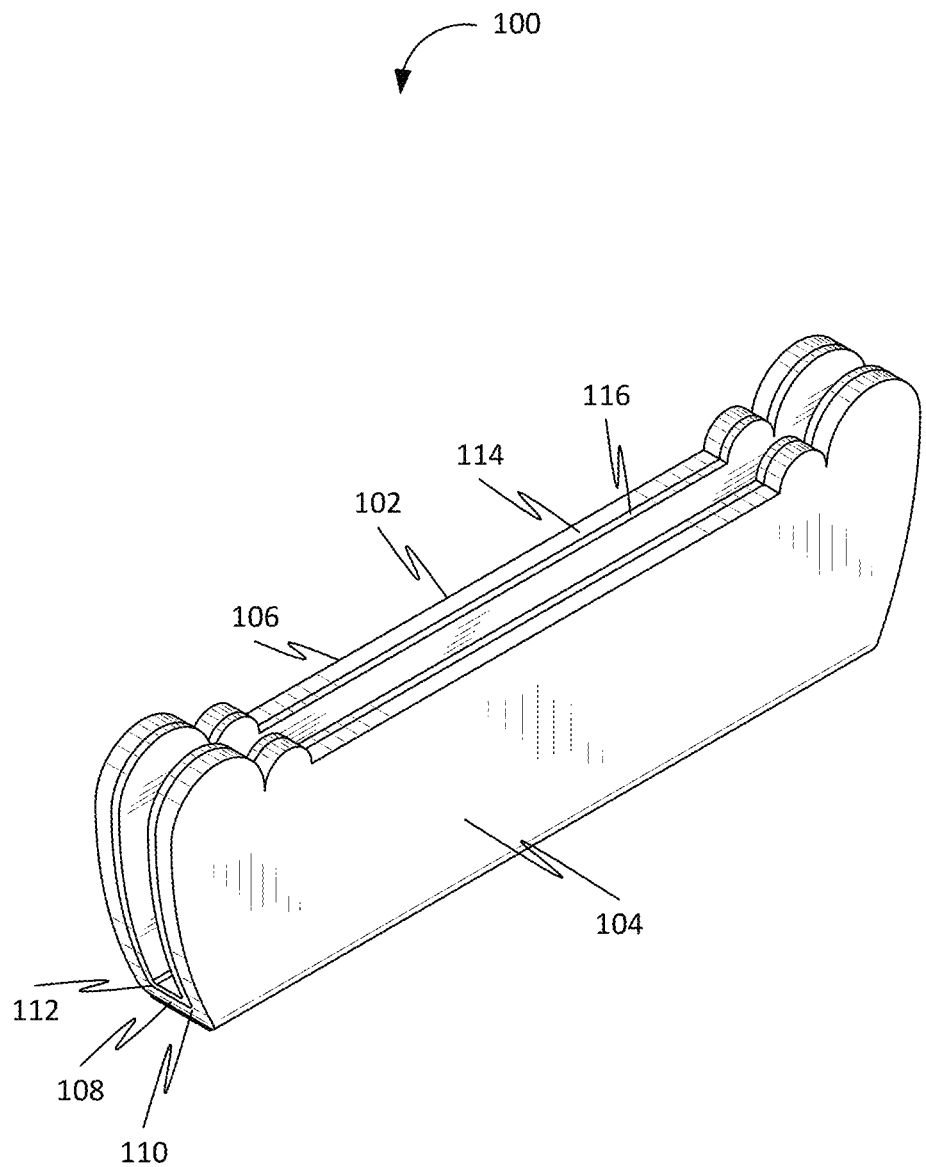
FIG. 1 is a top front perspective view of an article 100 for absorbing bodily discharges of a user, in accordance with some embodiments.

As a preliminary matter, it will readily be understood by one having ordinary skill in the relevant art that the present disclosure has broad utility and application. As should be understood, any embodiment may incorporate only one or a plurality of the above-disclosed aspects of the disclosure and may further incorporate only one or a plurality of the above-disclosed features. Furthermore, any embodiment discussed and identified as being "preferred" is considered to be part of a best mode contemplated for carrying out the embodiments of the present disclosure. Other embodiments also may be discussed for additional illustrative purposes in providing a full and enabling disclosure. Moreover, many embodiments, such as adaptations, variations, modifications, and equivalent arrangements, will be implicitly disclosed by the embodiments described herein and fall within the scope of the present disclosure.

Accordingly, while embodiments are described herein in detail in relation to one or more embodiments, it is to be understood that this disclosure is illustrative and exemplary of the present disclosure, and are made merely for the purposes of providing a full and enabling disclosure. The detailed disclosure herein of one or more embodiments is not intended, nor is to be construed, to limit the scope of patent protection afforded in any claim of a patent issuing here from, which scope is to be defined by the claims and the equivalents thereof. It is not intended that the scope of patent protection be defined by reading into any claim limitation found herein and/or issuing here from that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present disclosure. Accordingly, it is intended that the scope of patent protection is to be defined by the issued claim(s) rather than the description set forth herein.

Additionally, it is important to note that each term used herein refers to that which an ordinary artisan would understand such term to mean based on the contextual use of such term herein. To the extent that the meaning of a term used herein—as understood by the ordinary artisan based on the contextual use of such term—differs in any way from any particular dictionary definition of such term, it is intended that the meaning of the term as understood by the ordinary artisan should prevail.

Furthermore, it is important to note that, as used herein, "a" and "an" each generally denotes "at least one," but does not exclude a plurality unless the contextual use dictates otherwise. When used herein to join a list of items, "or" denotes "at least one of the items," but does not exclude a plurality of items of the list. Finally, when used herein to join a list of items, "and" denotes "all of the items of the list."

The following detailed description refers to the accompanying drawings. Wherever possible, the same reference numbers are used in the drawings and the following description to refer to the same or similar elements. While many embodiments of the disclosure may be described, modifications, adaptations, and other implementations are possible. For example, substitutions, additions, or modifications may be made to the elements illustrated in the drawings, and the methods described herein may be modified by substituting, reordering, or adding stages to the disclosed methods. Accordingly, the following detailed description does not limit the disclosure. Instead, the proper scope of the disclosure is defined by the claims found herein and/or issuing here from. The present disclosure contains headers. It should be understood that these headers are used as references and are not to be construed as limiting upon the subjected matter disclosed under the header.

The present disclosure includes many aspects and features. Moreover, while many aspects and features relate to, and are described in the context of an article for absorbing bodily discharges of a user, embodiments of the present disclosure are not limited to use only in this context.

OVERVIEW

Further, the present disclosure describes an article for absorbing bodily discharges of a user. Further, the article may be a sanitary leakage preventive fin (fin).

Further, the fin is attached to a pad (sanitary pad). Further, the fin is placed in a space between the buttocks. Further, the fin prevents the menstrual discharge from flowing out from the space between the buttocks creating a barrier and additional absorption. Further, the pad with the fin promotes a more secure fit to the body and prevents secretions (menstrual discharge) from leaking through empty spaces that can form between the body and the pad. Further, the fin includes thin wings with a soft upper surface and an adhesive lower surface for ensuring the reliable and comfortable attachment of the fin to the pad surface.

Further, the present disclosure describes an additional vertical element for feminine sanitary pads. Further, the additional vertical element is an auxiliary means of protection against leaks of menstrual discharge. Further, the additional vertical element is designed to prevent leakage and leakage of secretions (menstrual discharge) outside the pad during sleep or other situations associated with a horizontal body position. The additional vertical element is called the "fin" which is attached to the surface of the sanitary pad, namely to the central part of its back half in order to be located and held in the intergluteal space. In this way, the "fin" provides a barrier between the secretions and the wearer's underwear, preventing the secretions from leaking out through the free space between the buttocks, which is now filled with the "fin". The "fin" consists of an edge and two wings on the sides, with the help of which it is attached to the surface of the pad. The "fin" consists of two main layers: The upper covering layer which is designed to protect the skin from secretions and pass them to the second layer. Further, the upper covering layer is made from natural hypoallergenic materials. Further, the second layer is a bottom absorbent layer which is designed to absorb and retain secretions. Further, the bottom absorbent layer is made from loosely arranged cellulose, synthetic, cotton fibers (wadding), and other absorbent natural or synthetic materials.

Further, the present disclosure describes an additional vertical element for a feminine sanitary pad (pad), called a "fin". This fin is designed to prevent leaks and prevent secretions from flowing outside the pad, especially during horizontal body positioning, such as during sleep. The fin attaches to the center back of the pad and acts as a barrier between the discharges and the wearer's underwear. The fin consists of two main layers: a top protective layer to protect the skin from secretions and a lower absorbent layer to retain secretions.

Further, the present disclosure describes sanitary products for period hygiene. Further, the sanitary products may include a fin. Further, the fin is a special addition to period night pads. Further, the fin ensures 100% safety from blood leaks. Further, the fin may be attached to a period pad (such as a sanitary pad, an absorbent pad, a pad, etc.). Further, the fin has three sizes. Further, the fin has patterns embossed onto its surface from the inside and a sticky part on the outside. Further, the patterns go evenly into perforations comprised in the fin. Further, the sticky part goes on a back side of a middle portion of the fin. Further, the fin is attachable to the pad, specifically to its tail. Further, the pad includes a marking line on the pad to indicate to the user a location for sticking the fin. Further, the pad must be included in a package. Further, the pad may have three sizes. Further, the marking line shows a stick-to place on the pad. Further, the pad may be branded on the wings part of the pad. Further, a set of the sanitary products may include 30 pads, 30 fins, and 30 wet wipes. Further, the wet wipes have a neutral pH and no fragrance. Further, the wet wipe is non allergic.

Further, the sanitary products may include pads of 3 sizes, fins of 3 sizes, wet wipes with a neutral pH and no fragrance, branded packages for pads, branded packages for fins, branded packages for wipes, and branded boxes of 3 sizes. Further, the wet wipes may be hypo-allergic. Further, a branding of the pads goes on a contour part of the pads. Further, the pads include a colored place to show where the fins go. Further, the fins are branded with embossed print.

FIG. 1 is a top front perspective view of an article 100 for absorbing bodily discharges of a user, in accordance with some embodiments. Accordingly, the article 100 may include an absorbent element 102.

Further, the absorbent element 102 may be configured to be disposed in an intergluteal cleft of the user. Further, the absorbent element 102 may be continuously disposed along at least a portion of a length of the intergluteal cleft. Further, the absorbent element 102 may be disposed in the intergluteal cleft from a top side of the absorbent element 102. Further, the absorbent element 102 may include a sanitary leakage preventive fin (fin), an additional vertical element, a butterfly fin, etc. Further, the disposing of the absorbent element 102 in the intergluteal cleft may include closely fitting of the absorbent element 102 in the intergluteal cleft. Further, the user may include an individual, a person, a woman, etc. Further, the intergluteal cleft may be referred to as at least a portion of a body groove associated with a crotch of the user. Further, the body groove extends from an end (posterior end) of a vagina and/or a labia of the user to a coccyx of the user. Further, the absorbent element 102 may include a base portion 108, a first portion 104, and a second portion 106. Further, the first portion 104 and the second portion 106 may be shaped in a butterfly wing shape. Further, the first portion 104 may be a first wing, the second portion 106 may be a second wing, and the base portion 108 may be a rib (edge). Further, the base portion 108 may be rectangularly shaped. Further, each of the first portion 104 and the second portion 106 may be rectangularly shaped and include one or more curved projections along a periphery of each of the first portion 104 and the second portion 106 on a top side of each of the first portion 104 and the second portion 106. Further, the one or more curved projections may be outwardly convex projections with one or more curvatures and comprised in at least one end of the periphery of each of the first portion 104 and the second portion 106 on the top side of each of the first portion 104 and the second portion 106. Further, the one or more curved projections may be deformable and comprised of at least one deformable material such as cotton, etc. Further, each of the first portion 104 and the second portion 106 may be elastically and/or elastomerically deformable and comprised of at least one elastomeric foam such as nitrile rubber foam, polyethylene foam, silicone foam, etc. Further, the first portion 104 may be attached to the base portion 108 on a first side 110 of the base portion 108 and the second portion 106 may be attached to the base portion 108 on a second side 112 of the base portion 108. Further, the first side 110 opposes the second side 112. Further, each of the first portion 104 and the second portion 106 extends vertically away from the base portion 108. Further, each of the first portion 104 and the second portion 106 extends outwardly and vertically away from the base portion 108. Further, the absorbent element 102 may include an outer layer 114 and an inner layer 116. Further, the inner layer 116 may be disposed below the outer layer 114. Further, the outer layer 114 collects a bodily discharge of the user and the inner layer 116 absorbs the bodily discharge collected by the outer layer 114. Further, the bodily discharge may include secretion, menstrual blood, menstrual discharge, vaginal discharge, urine, etc. Further, the outer layer 114 may be comprised of natural hypoallergenic materials. Further, the inner layer 116 may be comprised of loosely arranged cellulose, synthetic, cotton fibers, and other absorbent natural or synthetic materials. Further, the collecting of the bodily discharge by the outer layer 114 may include collecting the bodily discharge running towards the intergluteal cleft to prevent a leakage of the bodily discharge from the intergluteal cleft while a body of the user may be in a supine position.

Figure 2:
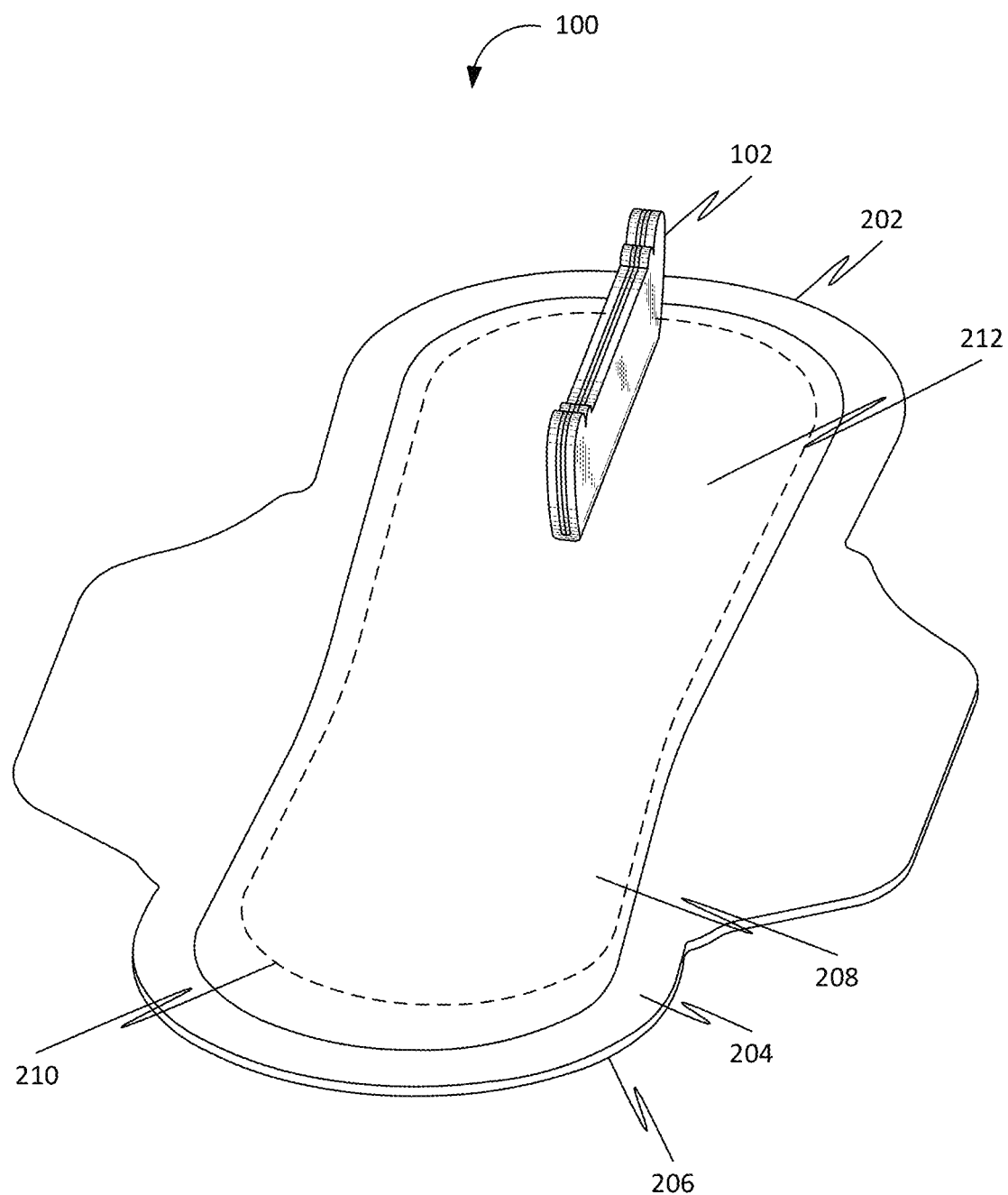
FIG. 2 is a top perspective view of the article 100 with the absorbent pad 202, in accordance with some embodiments.

In further embodiments, the article 100 may include an absorbent pad 202, as shown in FIG. 2. Further, the absorbent pad 202 may include a sanitary pad, a sanitary napkin, a pad, etc. Further, the absorbent pad 202 may be configured to be disposed in at least a portion of a crotch region of the user. Further, the crotch region corresponds to a crotch (undercarriage) of the user and may include a pubic region, a vaginal region, a perineum region, a gluteal region (outer gluteal region), etc. Further, the absorbent pad 202 may include a top layer 204, a bottom layer 206, and at least one absorbent material layer 208, as shown in FIG. 2. Further, the top layer 204 opposes at least the portion of the crotch region based on the disposing of the absorbent pad 202 in at least the portion of the crotch region. Further, the bottom layer 206 may be disposed below the top layer 204. Further, the at least one absorbent material layer 208 may be disposed between the top layer 204 and the bottom layer 206. Further, the absorbent element 102 may be attached to the absorbent pad 202. Further, the disposing of the absorbent element 102 in the intergluteal cleft may be based on the disposing of the absorbent pad 202 in at least the portion of the crotch region of the user. Further, the top layer 204 may be comprised of a liquid permeable sheet. Further, the bottom layer 206 may be comprised of a liquid impermeable sheet. Further, at least one absorbent material layer 208 may be comprised of a superabsorbent polymer (SAP). Further, the top layer 204 may be compliant, soft, flexible, etc. Further, the top layer 204 may be comprised of woven material, nonwoven material, polymeric material, porous foam, etc. Further, the top layer 204 may be comprised of natural fibers (cotton fibers, silk fibers, etc.), synthetic fibers (polyester fibers, polypropylene fibers, polyethylene fibers, etc.), etc. Further, the bottom layer 206 may be flexible, compliant, etc. Further, the bottom layer 206 may be comprised of woven material, nonwoven material, polymeric films, etc. Further, the bottom layer 206 may be comprised of natural fibers (cotton fibers, silk fibers, etc.), synthetic films (polyester films, polypropylene films, polyethylene films, etc.), etc.

Figure 3:
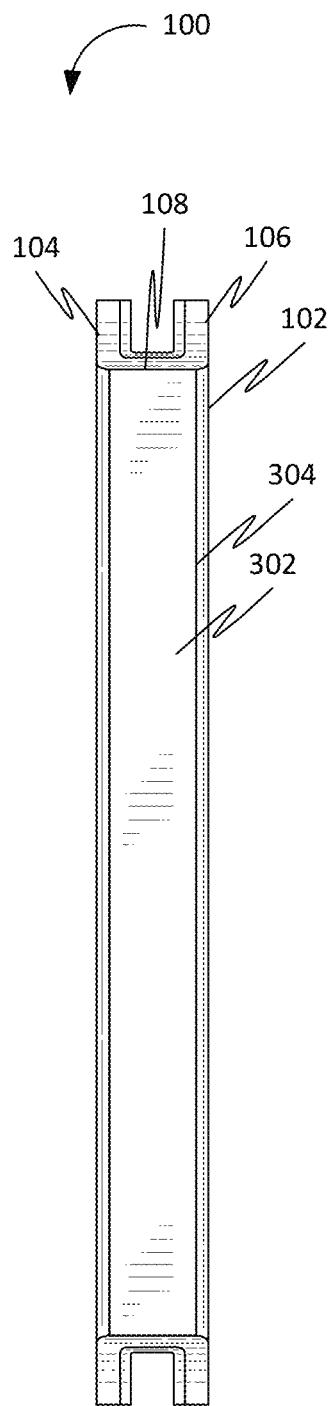
FIG. 3 is a bottom view of the article 100, in accordance with some embodiments.

Further, in an embodiment, the base portion 108 may include at least one attaching element 302, as shown in FIG. 3, disposed on a bottom side 304, as shown in FIG. 3, of the base portion 108. Further, the absorbent element 102 may be attached to the absorbent pad 202 based on the at least one attaching element 302. Further, in an embodiment, the absorbent element 102 may be detachably attached to the absorbent pad 202 based on the at least one attaching element 302. Further, the at least one attaching element 302 may include an adhesive layer comprising an adhesive, a reusable adhesive, a glue, etc.

Further, in an embodiment, the absorbent pad 202 may include a front portion 210 and a rear portion 212, as shown in FIG. 2. Further, the absorbent element 102 may be further attached to the rear portion 212 of the absorbent pad 202. Further, the front portion 210 opposes a vaginal region of the crotch region and the rear portion 212 opposes a perineal region of the crotch region and an intergluteal region of the crotch region.

Further, in an embodiment, the absorbent element 102 may be further centrally and longitudinally attached to the rear portion 212 of the absorbent pad 202.

Figure 4:
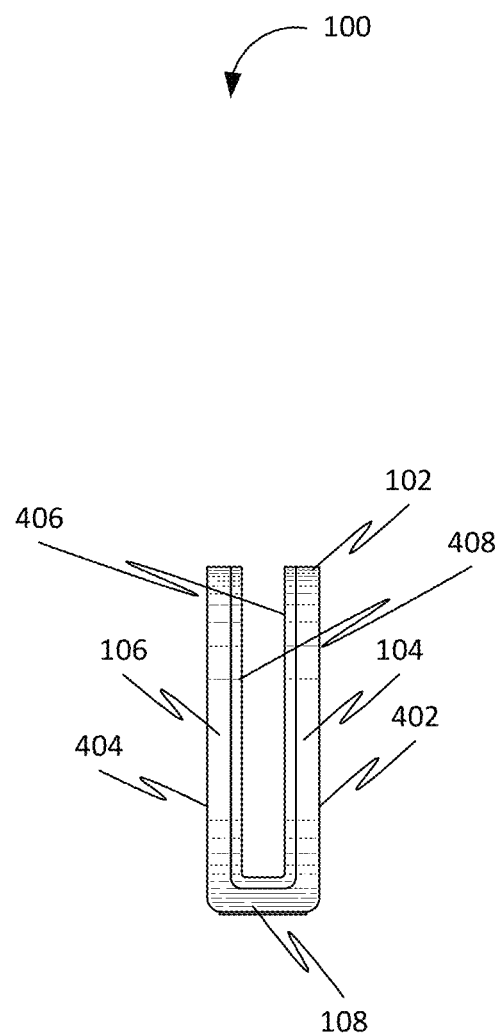
FIG. 4 is a left side view of the article 100, in accordance with some embodiments.

Further, in some embodiments, the first portion 104 corresponds to a right gluteal region of the user and the second portion 106 corresponds to a left gluteal region of the user. Further, the right gluteal region corresponds to a portion of an intergluteal region corresponding to a right buttock of the user. Further, the left gluteal region corresponds to a portion of the intergluteal region corresponding to a left buttock of the user. Further, each of the first portion 104 and the second portion 106 may include an outer surface (402 and 404) and an inner surface (406 and 408), as shown in FIG. 4. Further, the outer surface 402 of the first portion 104 faces the right gluteal region and the outer surface 404 of the second portion 106 faces the left gluteal region based on the disposing of the absorbent element 102 in the intergluteal cleft of the user.

Figure 5:
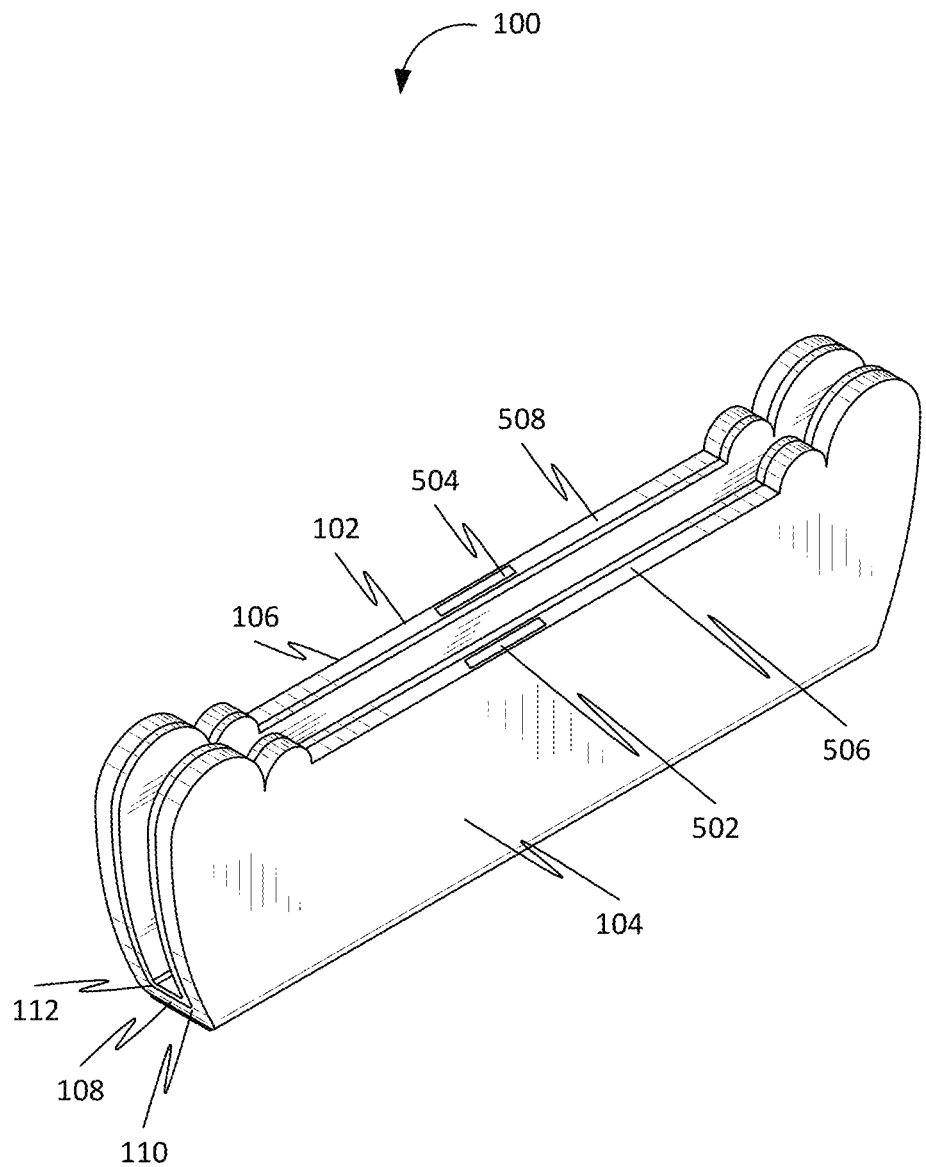
FIG. 5 is a top front perspective view of the article 100, in accordance with some embodiments.

Further, in some embodiments, the first portion 104 corresponds to a right gluteal region of the user and the second portion 106 corresponds to a left gluteal region of the user. Further, each of the first portion 104 and the second portion 106 may include an attaching element (502 and 504) disposed on a periphery (506 and 508), as shown in FIG. 5, of each of the first portion 104 and the second portion 106. Further, the attaching element 502 of the first portion 104 secures the first portion 104 on at least a portion of the right gluteal region. Further, the attaching element 504 of the second portion 106 secures the second portion 106 on at least a portion of the left gluteal region. Further, the attaching element (502 and 504) may include an adhesive layer comprising an adhesive, a reusable adhesive, etc.

Figure 6:
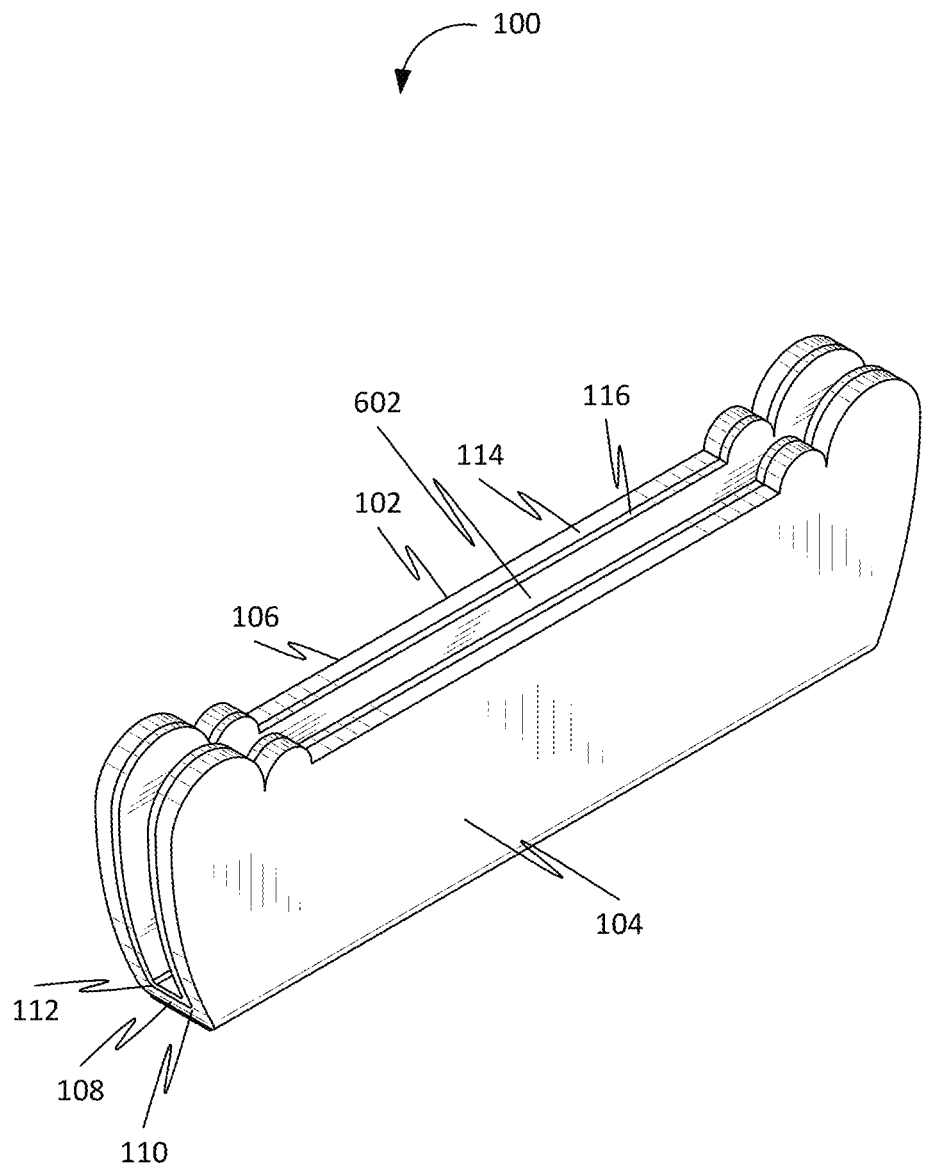
FIG. 6 is a top front perspective view of the article 100, in accordance with some embodiments.

Further, in some embodiments, the first portion 104 and the second portion 106 define a space 602, as shown in FIG. 6, between the first portion 104 and the second portion 106 based on the attaching of the first portion 104 to the first side 110 of the base portion 108 and the attaching of the second portion 106 to the second side 112 of the base portion 108. Further, an inner surface of the first portion 104, the second portion 106, and the base portion 108 define the space 602.

Figure 7:
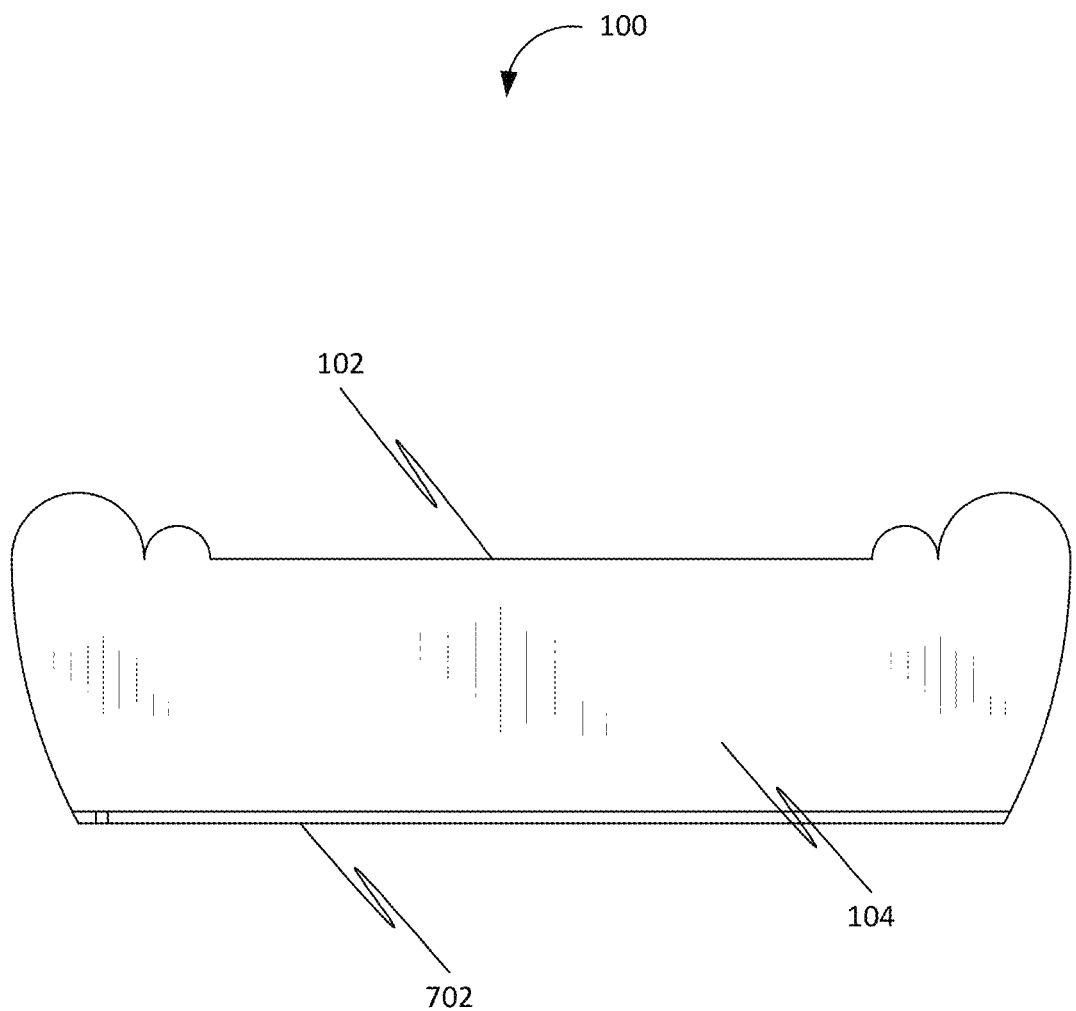
FIG. 7 is a front view of the article 100, in accordance with some embodiments.
Figure 8:
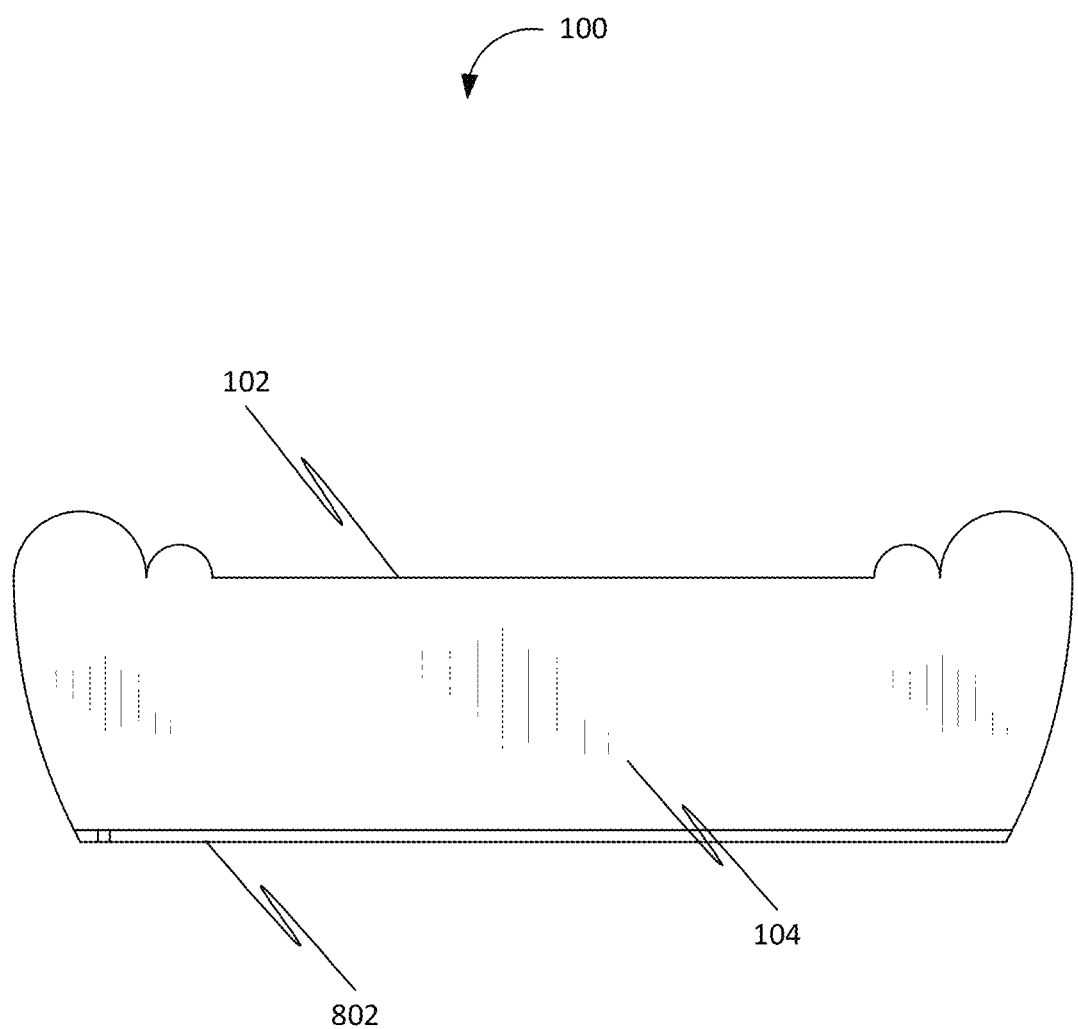
FIG. 8 is a rear view of the article 100, in accordance with some embodiments.

Further, in some embodiments, the first portion 104 may be flexibly attached to the first side 110 of the base portion 108 defining a first line of attachment 702, as shown in FIG. 7, and the second portion 106 may be flexibly attached to the second side 112 of the base portion 108 defining a second line of attachment 802, as shown in FIG. 8. Further, each of the first portion 104 and the second portion 106 may be configured to move between a plurality of positions about each of the first line of attachment 702 and the second line of attachment 802 based on the flexibly attaching of the first portion 104 to the first side 110 of the base portion 108 and the second portion 106 to the second side 112 of the base portion 108.

Further, in embodiment, the absorbent element 102 may be associated with a plurality of states. Further, the plurality of states may include an open state, a semi open state, a closed state, etc. Further, the plurality of states corresponds to the plurality of positions. Further, the plurality of positions may include a vertical position, an angled position, a horizontal position, etc. Further, the each of the first portion 104 and the second portion 106 may be perpendicular to the base portion 108 in the vertical position. Further, the vertical position corresponds to the closed state. Further, the each of the first portion 104 and the second portion 106 may form an obtuse angle with the base portion 108 in the angled position. Further, the angled position corresponds to the semi open state. Further, the each of the first portion 104 and the second portion 106 may be horizontal to the base portion 108 in the horizontal position. Further, the horizontal position corresponds to the open state.

Further, in an embodiment, the first portion 104 may be movably attached to the first side 110 of the base portion 108 and the second portion 106 may be flexibly attached to the second side 112 of the base portion 108. Further, each of the first portion 104 and the second portion 106 may be configured to move between a plurality of positions along the first line of attachment 702 and the second line of attachment 802 based on the movably attaching of the first portion 104 to the first side 110 of the base portion 108 and the second portion 106 to the second side 112 of the base portion 108. Further, the movably attaching may be based on a guideway slider assembly. Further, the guideway slider assembly may include a guideway and a slider. Further, the guideway may be comprised in a side edge of the base portion 108 corresponding to each of the first side 110 and the second side 112. Further, the slider may be comprised in a bottom edge of each of the first portion 104 and the second portion 106

Figure 11:
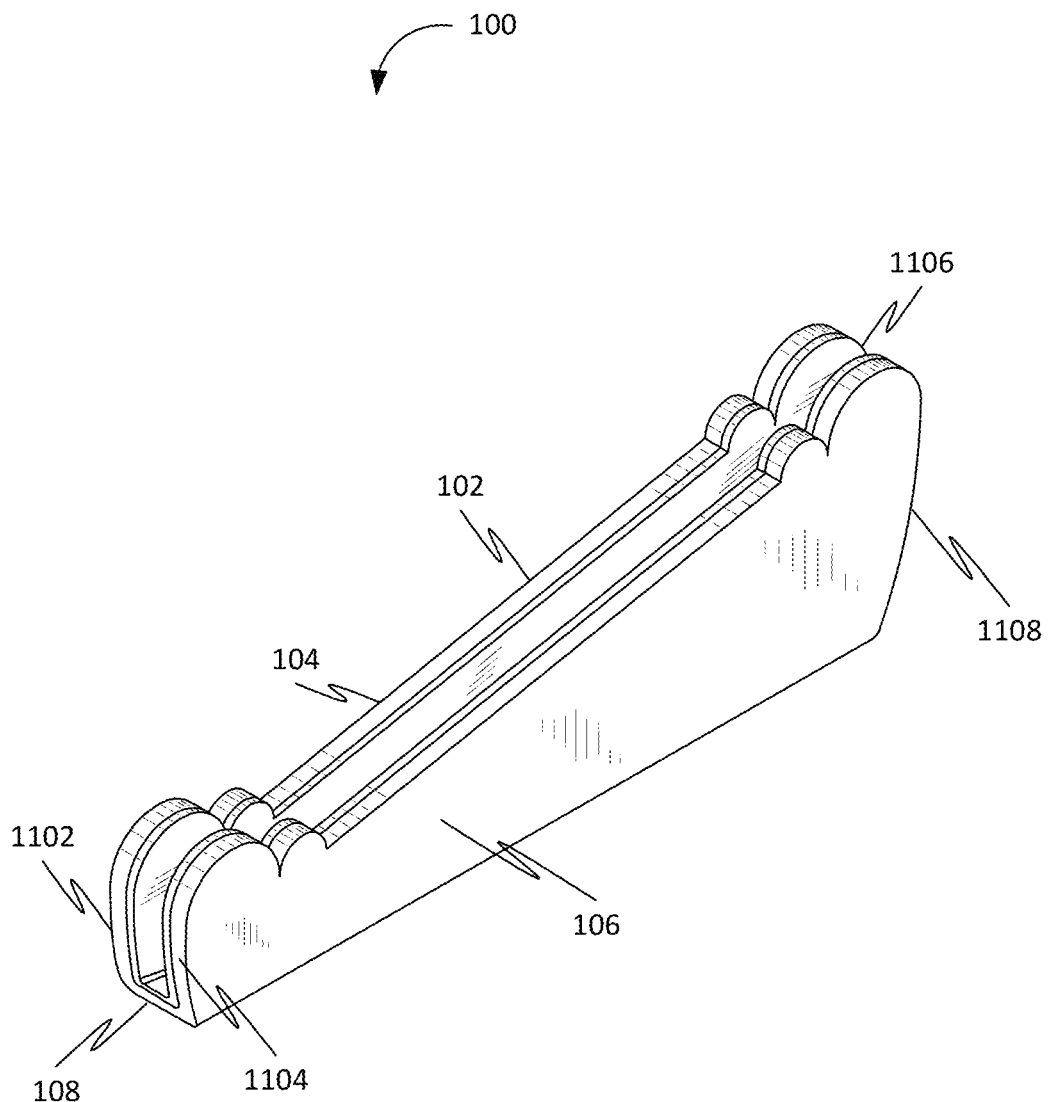
FIG. 11 is a top rear perspective view of the article 100, in accordance with some embodiments.

Further, in some embodiments, each of the first portion 104 and the second portion 106 may be characterized by a length and a width. Further, each of the first portion 104 and the second portion 106 extends between a first end (1102 and 1104) and a second end (1106 and 1108), as shown in FIG. 11. Further, the width of at least one of the first portion 104 and the second portion 106 progressively decreases from the second end (1106 and 1108) of at least one of the first portion 104 and the second portion 106 to the first end (1102 and 1104) of at least one of the first portion 104 and the second portion 106 along the length of at least one of the first portion 104 and the second portion 106. Further, the second end (1106 and 1108) of at least one of the first portion 104 and the second portion 106 may be disposed in a perineal region of the user and the first end (1102 and 1104) of at least one of the first portion 104 and the second portion 106 extend along the intergluteal cleft from the perineal region. Further, the width of at least one of the first portion 104 and the second portion 106 at the second end (1106 and 1108) may be greater than the width of at least one of the first portion 104 and the second portion 106 at the first end (1102 and 1104) by at least one percentage of the width of at least one of the first portion 104 and the second portion 106 at the first end (1102 and 1104). Further, the width of at least one of the first portion 104 and the second portion 106 corresponds to a width of the inner layer 116 and the outer layer 114. Further, the width of the inner layer 116 and the outer layer 114 corresponds to a capacity for the collecting and the absorbing of the bodily discharge.

Figure 12:
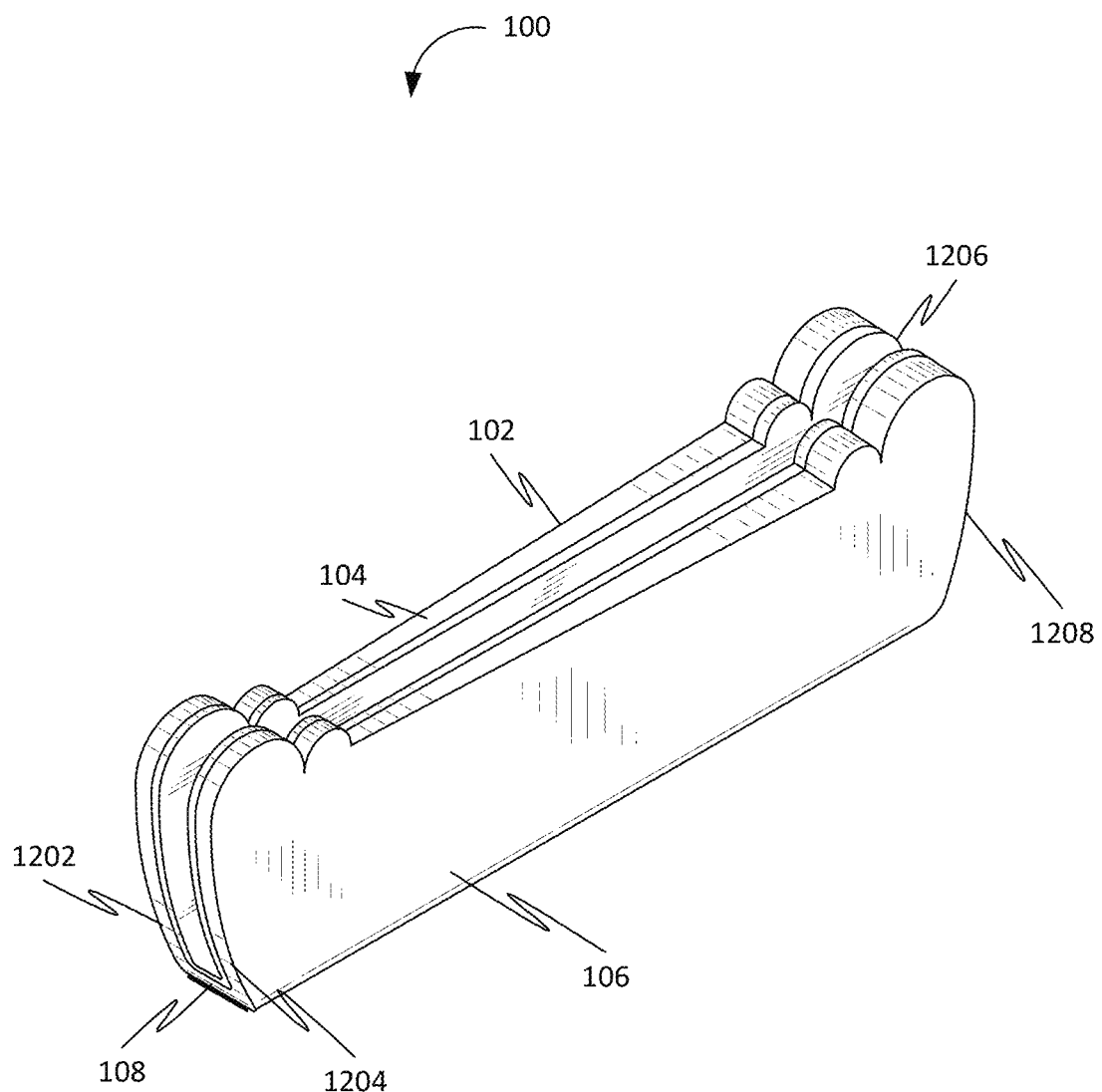
FIG. 12 is a top rear perspective view of the article 100, in accordance with some embodiments.

Further, in some embodiments, each of the first portion 104 and the second portion 106 may be characterized by a length and a thickness. Further, each of the first portion 104 and the second portion 106 extends between a first end (1202 and 1204) and a second end (1206 and 1208), as shown in FIG. 12. Further, the thickness of at least one of the first portion 104 and the second portion 106 progressively decreases from the second end (1206 and 1208) of at least one of the first portion 104 and the second portion 106 to the first end (1202 and 1204) of at least one of the first portion 104 and the second portion 106 along the length of at least one of the first portion 104 and the second portion 106. Further, the second end (1206 and 1208) of at least one of the first portion 104 and the second portion 106 may be disposed in a perineal region of the user and the first end (1202 and 1204) of at least one of the first portion 104 and the second portion 106 extend along the intergluteal cleft from the perineal region. Further, the thickness of at least one of the first portion 104 and the second portion 106 at the second end (1206 and 1208) may be greater than the thickness of at least one of the first portion 104 and the second portion 106 at the first end (1202 and 1204) by at least one percentage of the thickness of at least one of the first portion 104 and the second portion 106 at the first end (1202 and 1204). Further, the thickness of at least one of the first portion 104 and the second portion 106 corresponds to a thickness of the inner layer 116 and the outer layer 114. Further, the thickness of the inner layer 116 and the outer layer 114 corresponds to a capacity for the collecting and the absorbing of the bodily discharge.

FIG. 2 is a top perspective view of the article 100 with the absorbent pad 202, in accordance with some embodiments. Further, the absorbent element 102 may be associated with a closed state.

FIG. 3 is a bottom view of the article 100, in accordance with some embodiments.

FIG. 4 is a left side view of the article 100, in accordance with some embodiments.

FIG. 5 is a top front perspective view of the article 100, in accordance with some embodiments.

FIG. 6 is a top front perspective view of the article 100, in accordance with some embodiments.

FIG. 7 is a front view of the article 100, in accordance with some embodiments.

FIG. 8 is a rear view of the article 100, in accordance with some embodiments.

Figure 9:
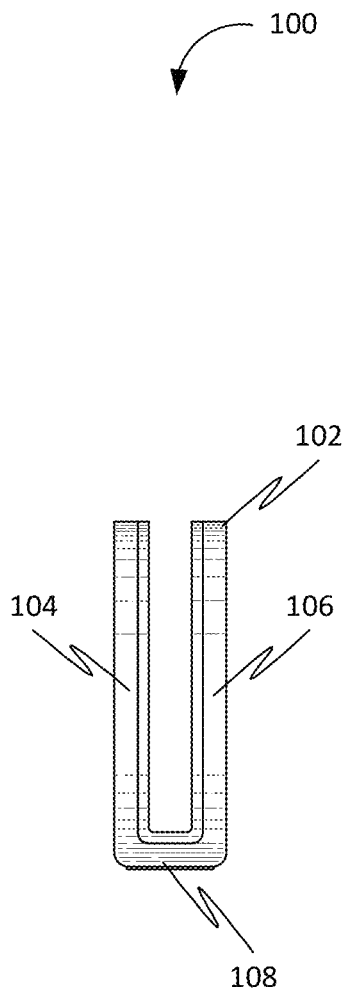
FIG. 9 is a right side view of the article 100, in accordance with some embodiments.

FIG. 9 is a right side view of the article 100, in accordance with some embodiments.

Figure 10:
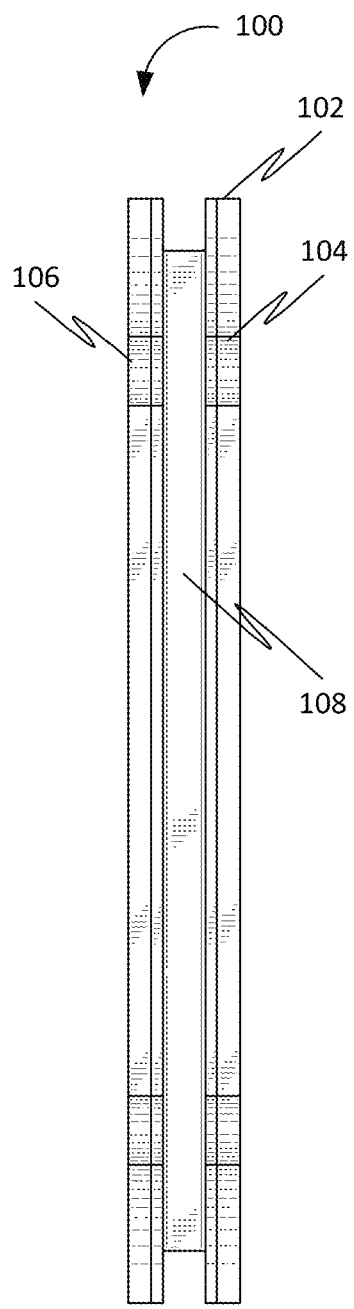
FIG. 10 is a top view of the article 100, in accordance with some embodiments.

FIG. 10 is a top view of the article 100, in accordance with some embodiments.

FIG. 11 is a top rear perspective view of the article 100, in accordance with some embodiments.

FIG. 12 is a top rear perspective view of the article 100, in accordance with some embodiments.

Figure 13:
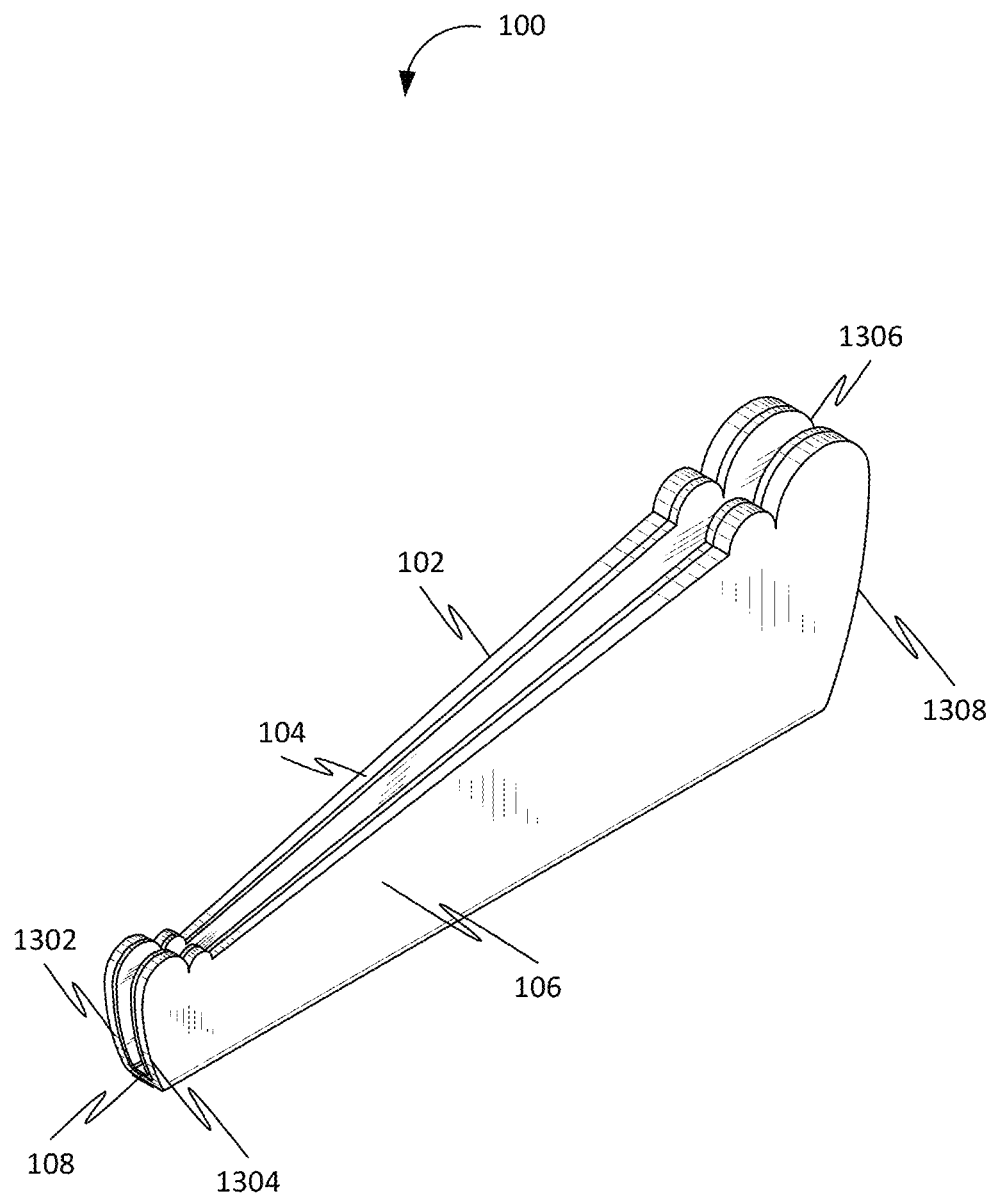
FIG. 13 is a top rear perspective view of the article 100, in accordance with some embodiments.

FIG. 13 is a top rear perspective view of the article 100, in accordance with some embodiments. Further, each of the first portion 104 and the second portion 106 may be characterized by a length, a width, and a thickness. Further, each of the first portion 104 and the second portion 106 extends between a first end (1302 and 1304) and a second end (1306 and 1308), as shown in FIG. 13. Further, the thickness and the width of at least one of the first portion 104 and the second portion 106 progressively decreases from the second end (1306 and 1308) of at least one of the first portion 104 and the second portion 106 to the first end (1302 and 1304) of at least one of the first portion 104 and the second portion 106 along the length of at least one of the first portion 104 and the second portion 106. Further, the second end (1306 and 1308) of at least one of the first portion 104 and the second portion 106 may be disposed in a perineal region of the user and the first end (1302 and 1304) of at least one of the first portion 104 and the second portion 106 extend along the intergluteal cleft from the perineal region. Further, the width and thickness of at least one of the first portion 104 and the second portion 106 at the second end (1306 and 1308) may be greater than the width and the thickness of at least one of the first portion 104 and the second portion 106 at the first end (1302 and 1304) by at least one percentage of the width and the thickness of at least one of the first portion 104 and the second portion 106 at the first end (1302 and 1304).

Figure 14:
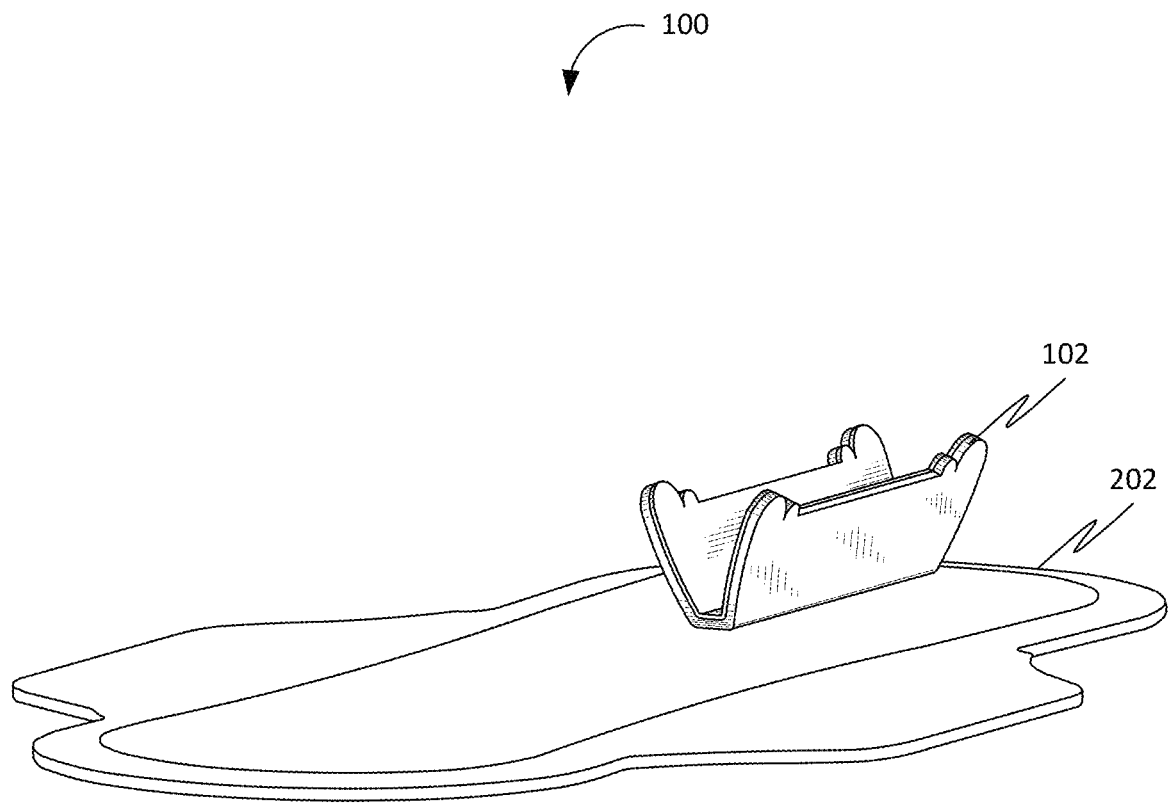
FIG. 14 is a front perspective view of the article 100 with the absorbent pad 202, in accordance with some embodiments.

FIG. 14 is a front perspective view of the article 100 with the absorbent pad 202, in accordance with some embodiments. Further, the absorbent element 102 may be associated with a semi open state.

Figure 15:
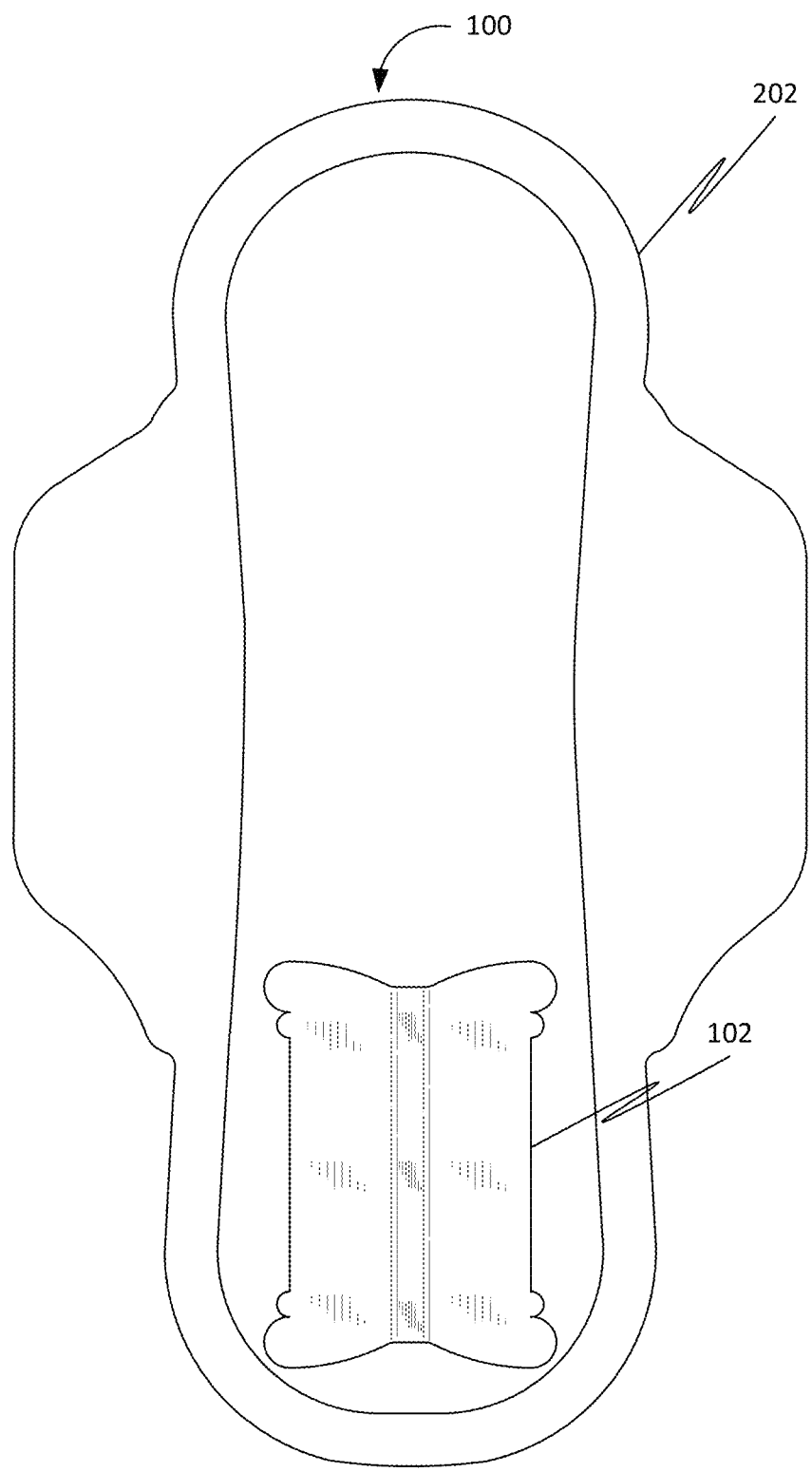
FIG. 15 is a top view of the article 100 with the absorbent pad 202, in accordance with some embodiments.

FIG. 15 is a top view of the article 100 with the absorbent pad 202, in accordance with some embodiments. Further, the absorbent element 102 may be associated with an open state.

Figure 16:
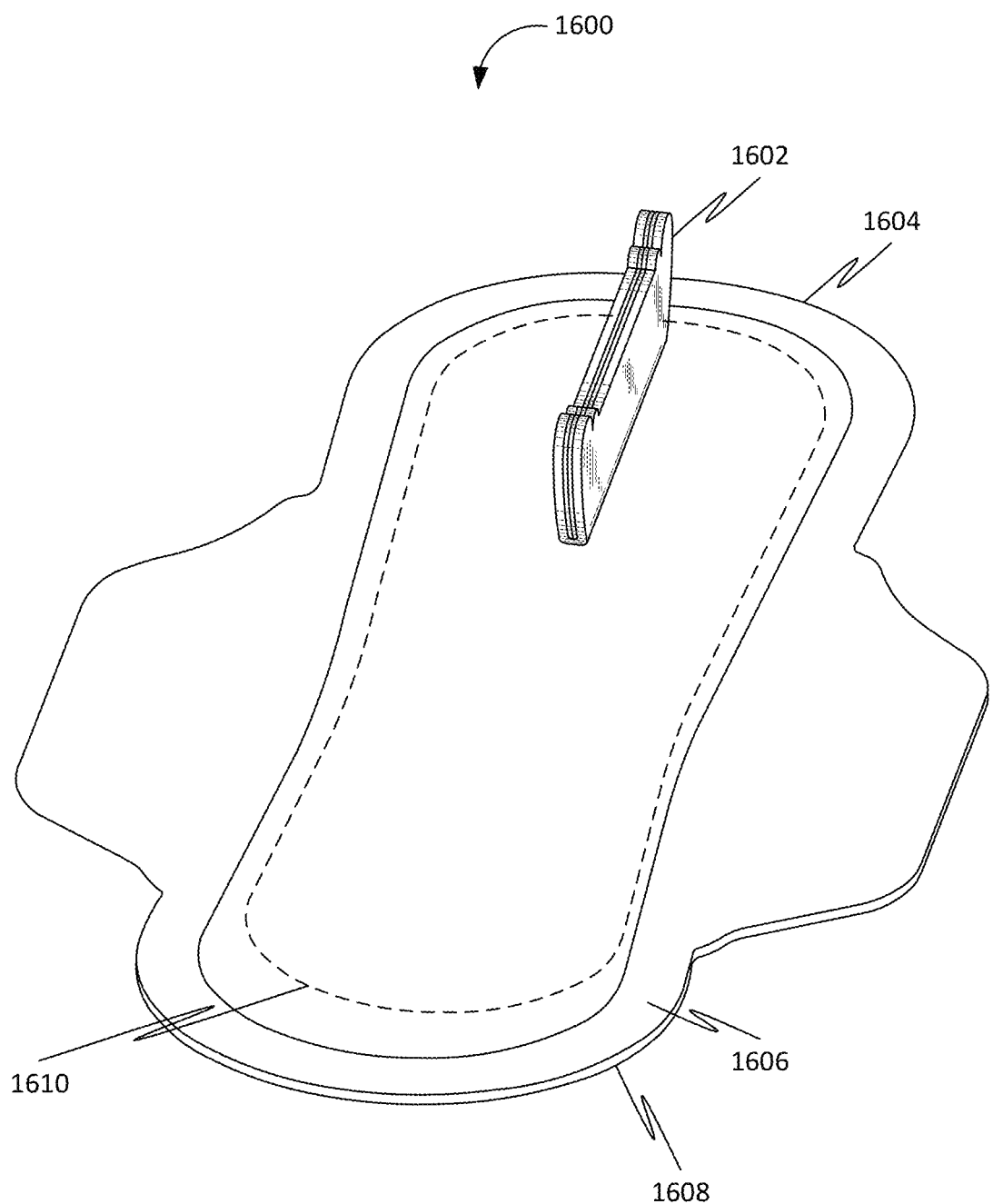
FIG. 16 is a top perspective view of an article 1600 for absorbing bodily discharges of a user, in accordance with some embodiments.

FIG. 16 is a top perspective view of an article 1600 for absorbing bodily discharges of a user, in accordance with some embodiments. Accordingly, the article 1600 may include an absorbent element 1602 and an absorbent pad 1604.

Figure 17:
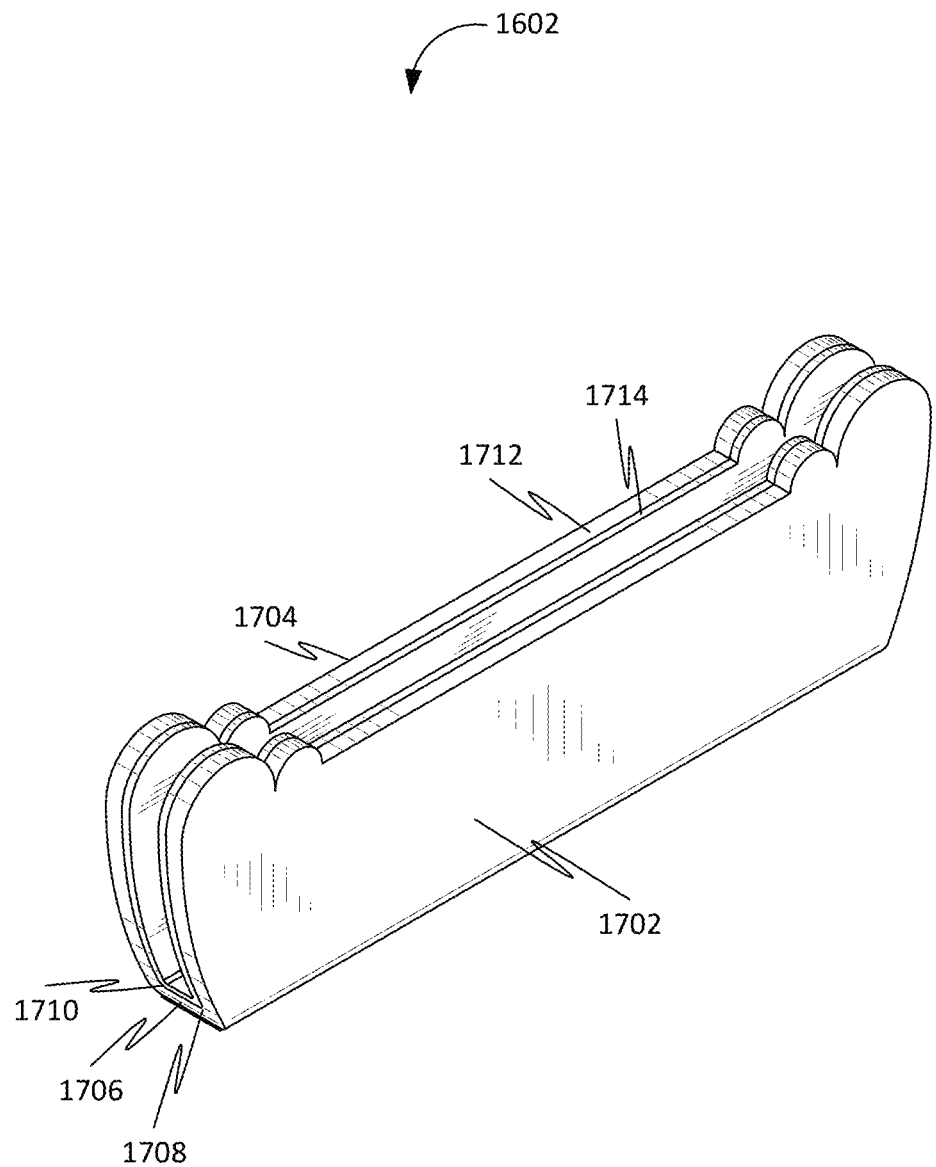
FIG. 17 is a top front perspective view of the absorbent element 1602 of the article 1600, in accordance with some embodiments.

Further, the absorbent element 1602 may be configured to be disposed in an intergluteal cleft of the user. Further, the absorbent element 1602 may include a base portion 1706, a first portion 1702, and a second portion 1704, as shown in FIG. 17. Further, the first portion 1702 may be attached to the base portion 1706 on a first side 1708 of the base portion 1706 and the second portion 1704 may be attached to the base portion 1706 on a second side 1710 of the base portion 1706. Further, the first side 1708 opposes the second side 1710. Further, each of the first portion 1702 and the second portion 1704 extends vertically away from the base portion 1706. Further, the absorbent element 1602 may include an outer layer 1712 and an inner layer 1714, as shown in FIG. 17. Further, the inner layer 1714 may be disposed below the outer layer 1712. Further, the outer layer 1712 collects a bodily discharge of the user and the inner layer 1714 absorbs the bodily discharge collected by the outer layer 1712.

Further, the absorbent pad 1604 may be configured to be disposed in at least a portion of a crotch region of the user. Further, the absorbent pad 1604 may include a top layer 1606, a bottom layer 1608, and at least one absorbent material layer 1610. Further, the top layer 1606 opposes at least the portion of the crotch region based on the disposing of the absorbent pad 1604 in at least the portion of the crotch region. Further, the bottom layer 1608 may be disposed below the top layer 1606. Further, the at least one absorbent material layer 1610 may be disposed between the top layer 1606 and the bottom layer 1608. Further, the absorbent element 1602 may be attached to the absorbent pad 1604. Further, the disposing of the absorbent element 1602 in the intergluteal cleft may be based on the disposing of the absorbent pad 1604 in at least the portion of the crotch region of the user.

Further, in some embodiments, the base portion 1706 may include at least one attaching element disposed on a bottom side of the base portion 1706. Further, the absorbent element 1602 may be attached to the absorbent pad 1604 based on the at least one attaching element.

Further, in some embodiments, the absorbent pad 1604 may include a front portion and a rear portion. Further, the absorbent element 1602 may be further attached to the rear portion of the absorbent pad 1604.

Further, in some embodiments, the first portion 1702 corresponds to a right gluteal region of the user and the second portion 1704 corresponds to a left gluteal region of the user. Further, each of the first portion 1702 and the second portion 1704 may include an outer surface and an inner surface. Further, the outer surface of the first portion 1702 faces the right gluteal region and the outer surface of the second portion 1704 faces the left gluteal region based on the disposing of the absorbent element 1602 in the intergluteal cleft of the user.

Further, in some embodiments, the first portion 1702 corresponds to a right gluteal region of the user and the second portion 1704 corresponds to a left gluteal region of the user. Further, each of the first portion 1702 and the second portion 1704 may include an attaching element disposed on a periphery of each of the first portion 1702 and the second portion 1704. Further, the attaching element of the first portion 1702 secures the first portion 1702 on at least a portion of the right gluteal region. Further, the attaching element of the second portion 1704 secures the second portion 1704 on at least a portion of the left gluteal region.

Further, in some embodiments, the first portion 1702 and the second portion 1704 define a space between the first portion 1702 and the second portion 1704 based on the attaching of the first portion 1702 to the first side 1708 of the base portion 1706 and the attaching of the second portion 1704 to the second side 1710 of the base portion 1706.

Further, in some embodiments, the first portion 1702 may be flexibly attached to the first side 1708 of the base portion 1706 defining a first line of attachment and the second portion 1704 may be flexibly attached to the second side 1710 of the base portion 1706 defining a second line of attachment. Further, each of the first portion 1702 and the second portion 1704 may be configured to move between a plurality of positions about each of the first line of attachment and the second line of attachment based on the flexibly attaching of the first portion 1702 to the first side 1708 of the base portion 1706 and the second portion 1704 to the second side 1710 of the base portion 1706.

Further, in some embodiments, each of the first portion 1702 and the second portion 1704 may be characterized by a length and a width. Further, each of the first portion 1702 and the second portion 1704 extends between a first end and a second end. Further, the width of at least one of the first portion 1702 and the second portion 1704 progressively decreases from the second end of at least one of the first portion 1702 and the second portion 1704 to the first end of at least one of the first portion 1702 and the second portion 1704 along the length of at least one of the first portion 1702 and the second portion 1704.

FIG. 17 is a top front perspective view of the absorbent element 1602 of the article 1600, in accordance with some embodiments.

Figure 18:
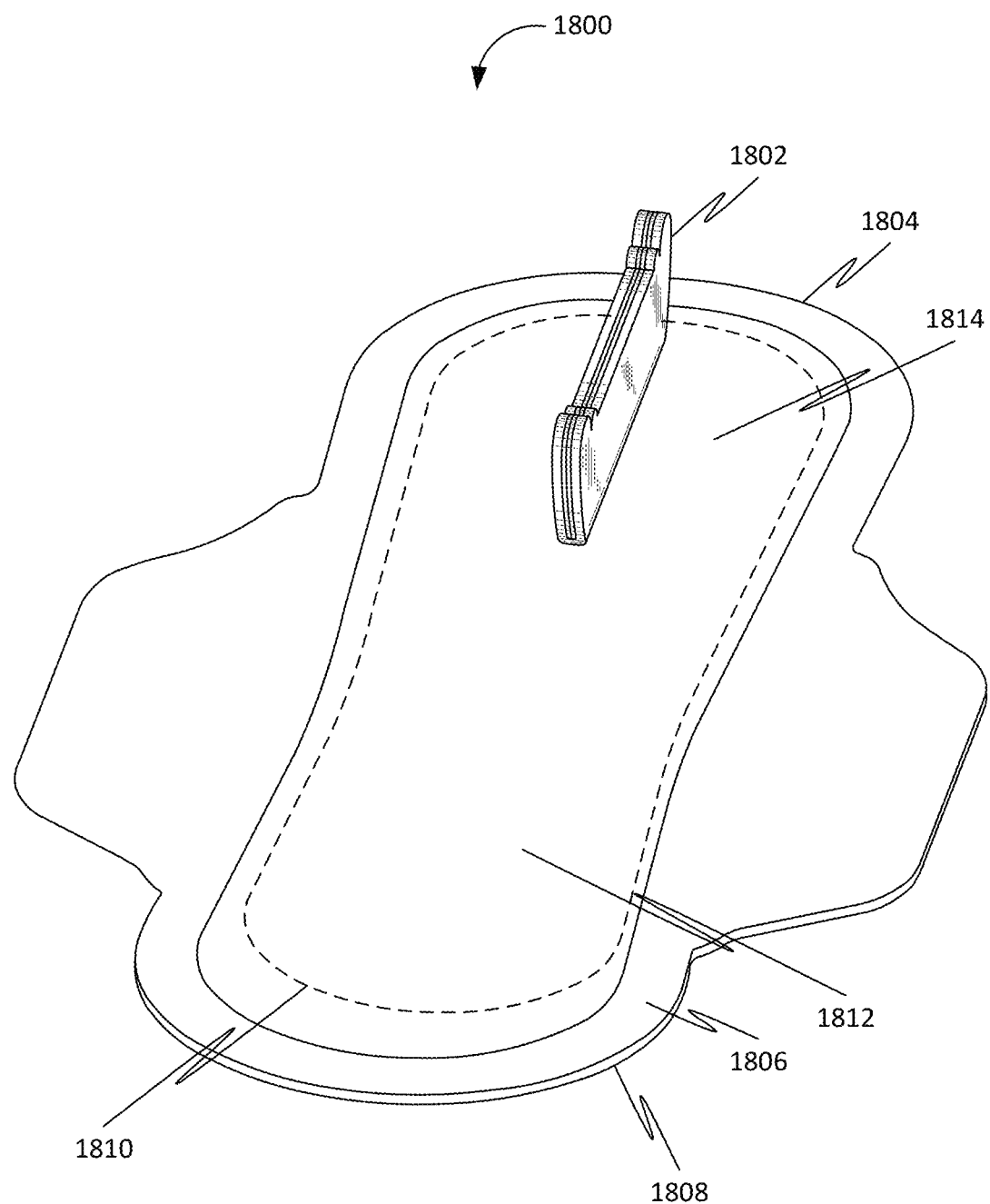
FIG. 18 is a top perspective view of an article 1800 for absorbing bodily discharges of a user, in accordance with some embodiments.

FIG. 18 is a top perspective view of an article 1800 for absorbing bodily discharges of a user, in accordance with some embodiments. Accordingly, the article 1800 may include an absorbent element 1802 and an absorbent pad 1804.

Figure 19:
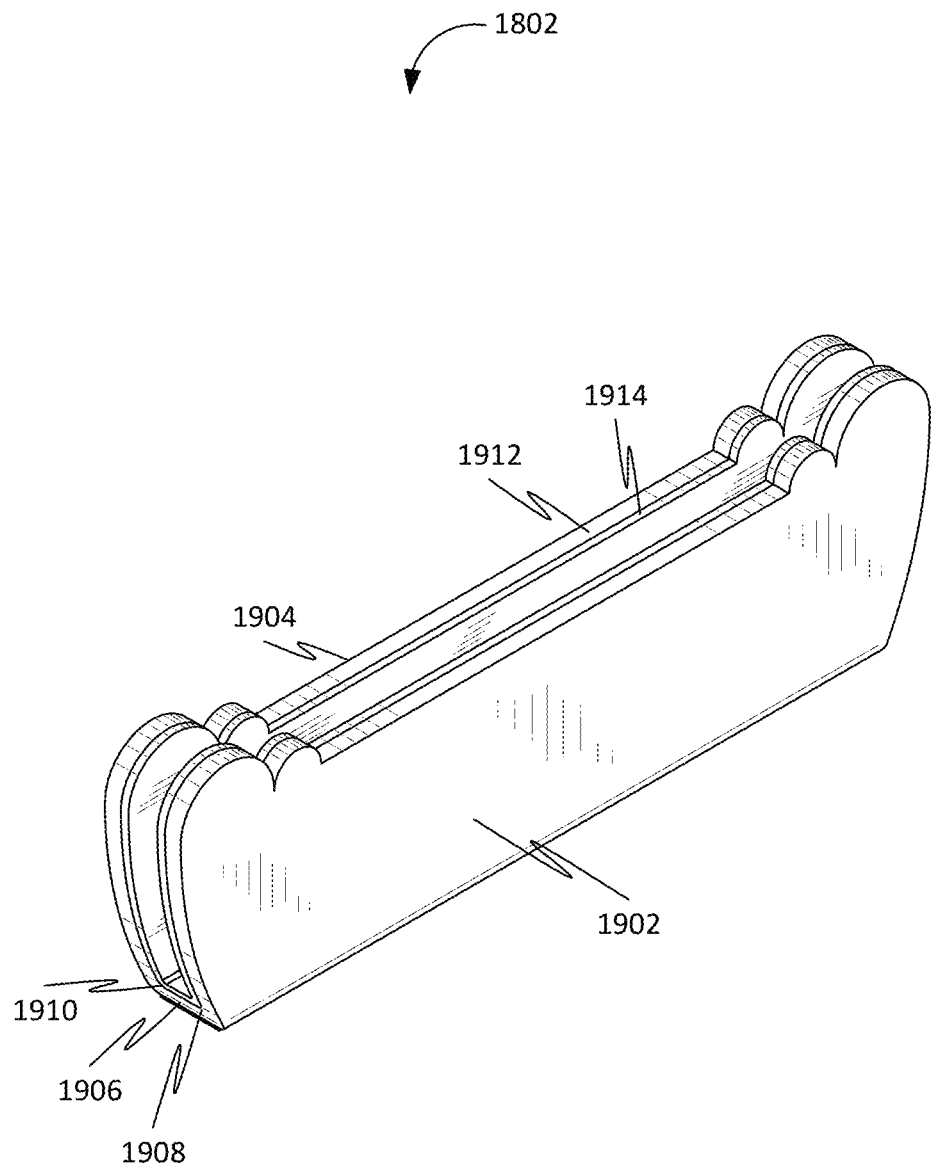
FIG. 19 is a top front perspective view of the absorbent element 1802 of the article 1800, in accordance with some embodiments.

Further, the absorbent element 1802 may be configured to be disposed in an intergluteal cleft of the user. Further, the absorbent element 1802 may include a base portion 1906, a first portion 1902, and a second portion 1904, as shown in FIG. 19. Further, the first portion 1902 may be attached to the base portion 1906 on a first side 1908 of the base portion 1906 and the second portion 1904 may be attached to the base portion 1906 on a second side 1910 of the base portion 1906. Further, the first side 1908 opposes the second side 1910. Further, each of the first portion 1902 and the second portion 1904 extends vertically away from the base portion 1906. Further, the absorbent element 1802 may include an outer layer 1912 and an inner layer 1914, as shown in FIG. 19. Further, the inner layer 1914 may be disposed below the outer layer 1912. Further, the outer layer 1912 collects a bodily discharge of the user and the inner layer 1914 absorbs the bodily discharge collected by the outer layer 1912.

Further, the absorbent pad 1804 may be configured to be disposed in at least a portion of a crotch region of the user. Further, the absorbent pad 1804 may include a top layer 1806, a bottom layer 1808, and at least one absorbent material layer 1810. Further, the top layer 1806 opposes at least the portion of the crotch region based on the disposing of the absorbent pad 1804 in at least the portion of the crotch region. Further, the bottom layer 1808 may be disposed below the top layer 1806. Further, the at least one absorbent material layer 1810 may be disposed between the top layer 1806 and the bottom layer 1808. Further, the absorbent element 1802 may be attached to the absorbent pad 1804. Further, the disposing of the absorbent element 1802 in the intergluteal cleft may be based on the disposing of the absorbent pad 1804 in at least the portion of the crotch region of the user. Further, the absorbent pad 1804 may include a front portion 1812 and a rear portion 1814. Further, the absorbent element 1802 may be attached to the rear portion 1814 of the absorbent pad 1804. Further, the absorbent element 1802 may be further centrally and longitudinally attached to the rear portion 1814 of the absorbent pad 1804.

FIG. 19 is a top front perspective view of the absorbent element 1802 of the article 1800, in accordance with some embodiments.

Figure 20:
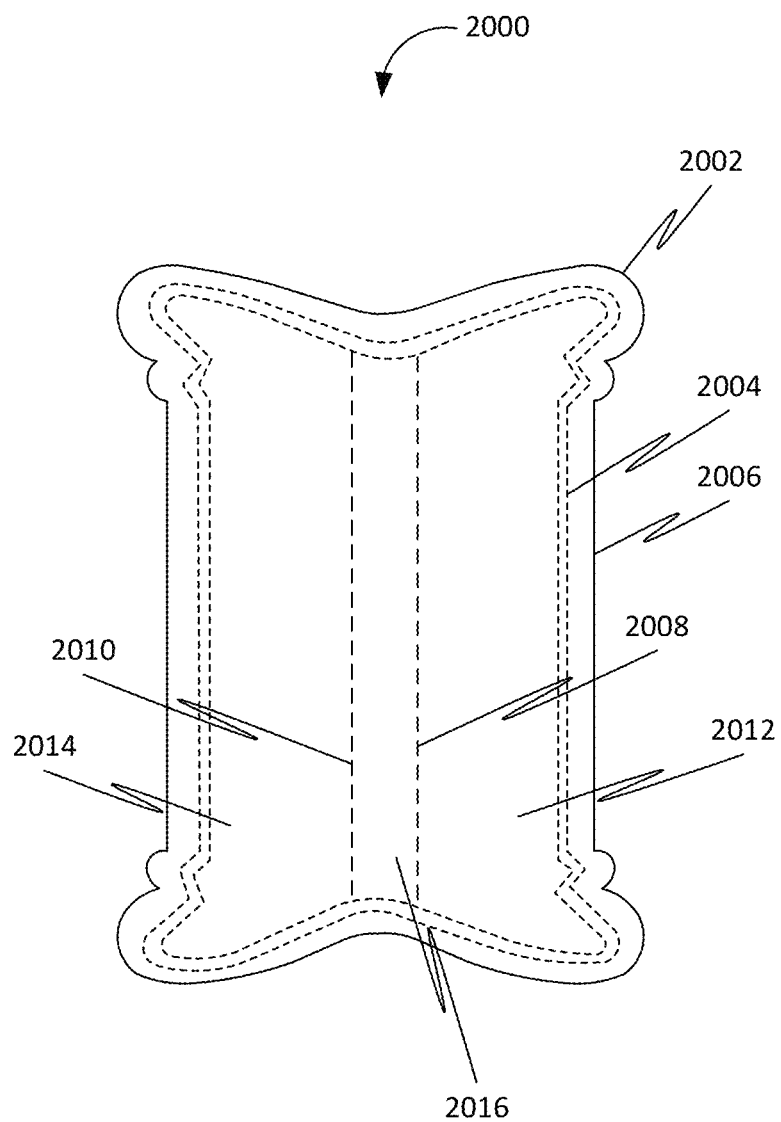
FIG. 20 is a top view of an article 2000 for absorbing bodily discharges of a user, in accordance with some embodiments.

FIG. 20 is a top view of an article 2000 for absorbing bodily discharges of a user, in accordance with some embodiments. Accordingly, the article 2000 may include an absorbent element 2002. Further, the absorbent element 2002 may include a perforated region 2004 along a periphery 2006 of the absorbent element 2002. Further, the perforated region 2004 may include a plurality of perforations of a specific size. Further, the absorbent element 2002 may include a plurality of lines 2008-2010 longitudinally extending along a length of the absorbent element 2002 defining a first portion 2012, a second portion 2014, and a base portion (central portion, middle portion, etc.) 2016. Further, the plurality of lines 2008-2010 may be folding lines. Further, the absorbent element 2002 may be folded about the plurality of lines 2008-2010 for transitioning the absorbent element 2002 between a plurality of states. Further, the plurality of states may include an open state, a closed state, a semi open state, etc. Further, the absorbent element 2002 may be shaped in a butterfly shape. Further, the butterfly shape may include two butterfly wings and a central portion between the two butterfly wings. Further, a shape of the first portion 2012 and the second portion 2014 corresponds to the two butterfly wings. Further, a shape of the central portion corresponds to the base portion 2016.

Figure 22:
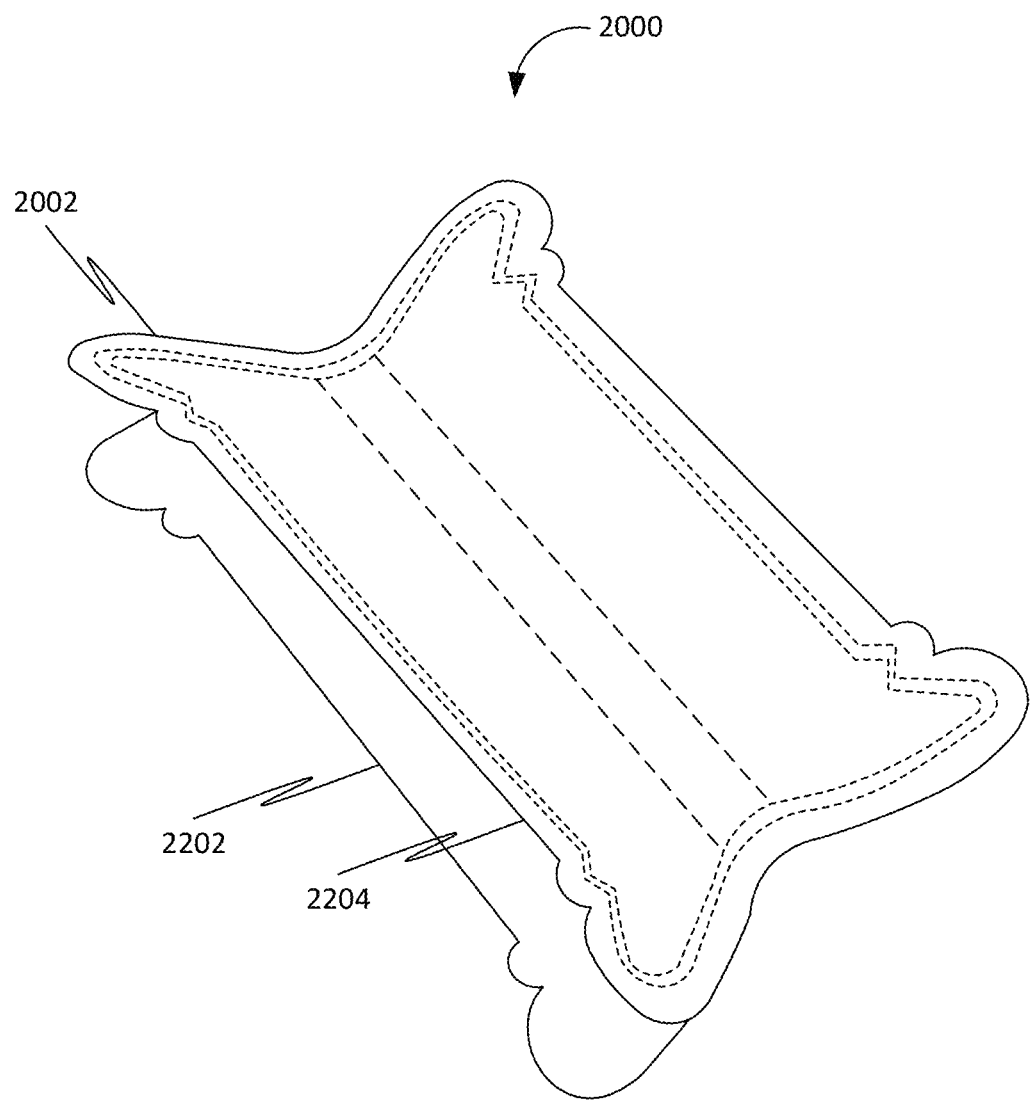
FIG. 22 is a top perspective view of the article 2000 comprising the backsheet 2202 with the absorbent element 2002, in accordance with some embodiments.

Further, in some embodiments, the absorbent element 2002 may include a backsheet 2202, as shown in FIG. 22, attached to a rear surface of the base portion 2016. Further, the backsheet 2202 may be shaped in the butterfly shape. Further, the backsheet 2202 may be a layer of adhesive paper attached to a rear side 2204, as shown in FIG. 22, of the absorbent element 2002. Further, the backsheet 2202 may be attached to the rear surface of the base portion 2016 based on a sticky material disposed on the rear surface of the base portion 2016. Further, the sticky material may include an adhesive, a reusable adhesive, a glue, etc.

Figure 23:
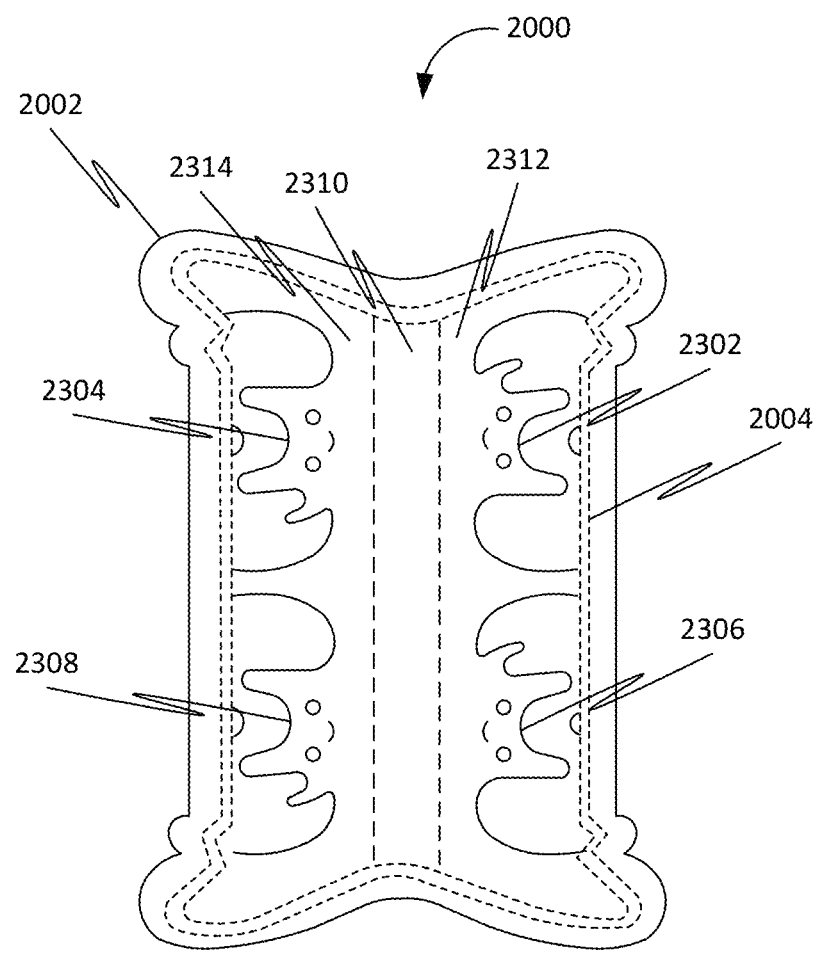
FIG. 23 is a top view of the article 2000, in accordance with some embodiments.

Further, in some embodiments, the absorbent element 2002 may include at least one pair of patterns (2302-2304 and 2306-2308), as shown in FIG. 23, embossed on a top surface 2310, as shown in FIG. 23, of the absorbent element 2002. Further, the at least one pair of patterns (2302-2304 and 2306-2308) may include at least one first pattern (2302 and 2306) and at least one second pattern (2304 and 2308), as shown in FIG. 23. Further, the at least one second pattern (2304 and 2308) may be a mirror of the at least one first pattern (2302 and 2306). Further, the at least one first pattern (2302 and 2306) may be embossed on a top surface 2312 of the first portion 2012 and the at least one second pattern (2304 and 2308) may be embossed on a top surface 2314 of the second portion 2014. Further, at least one of the at least one first pattern (2302 and 2306) and the at least one second pattern (2304 and 2308) goes evenly into at least one of the perforated region 2004 corresponding to at least one of the first portion 2012 and the second portion 2014. Further, at least one of the at least one first pattern (2302 and 2306) and the at least one second pattern (2304 and 2308) may be embossed on the top surface (2312 and 2314) of at least one of the first portion 2012 and the second portion 2014 from an interior of at least one of the first portion 2012 and the second portion 2014.

Figure 24:
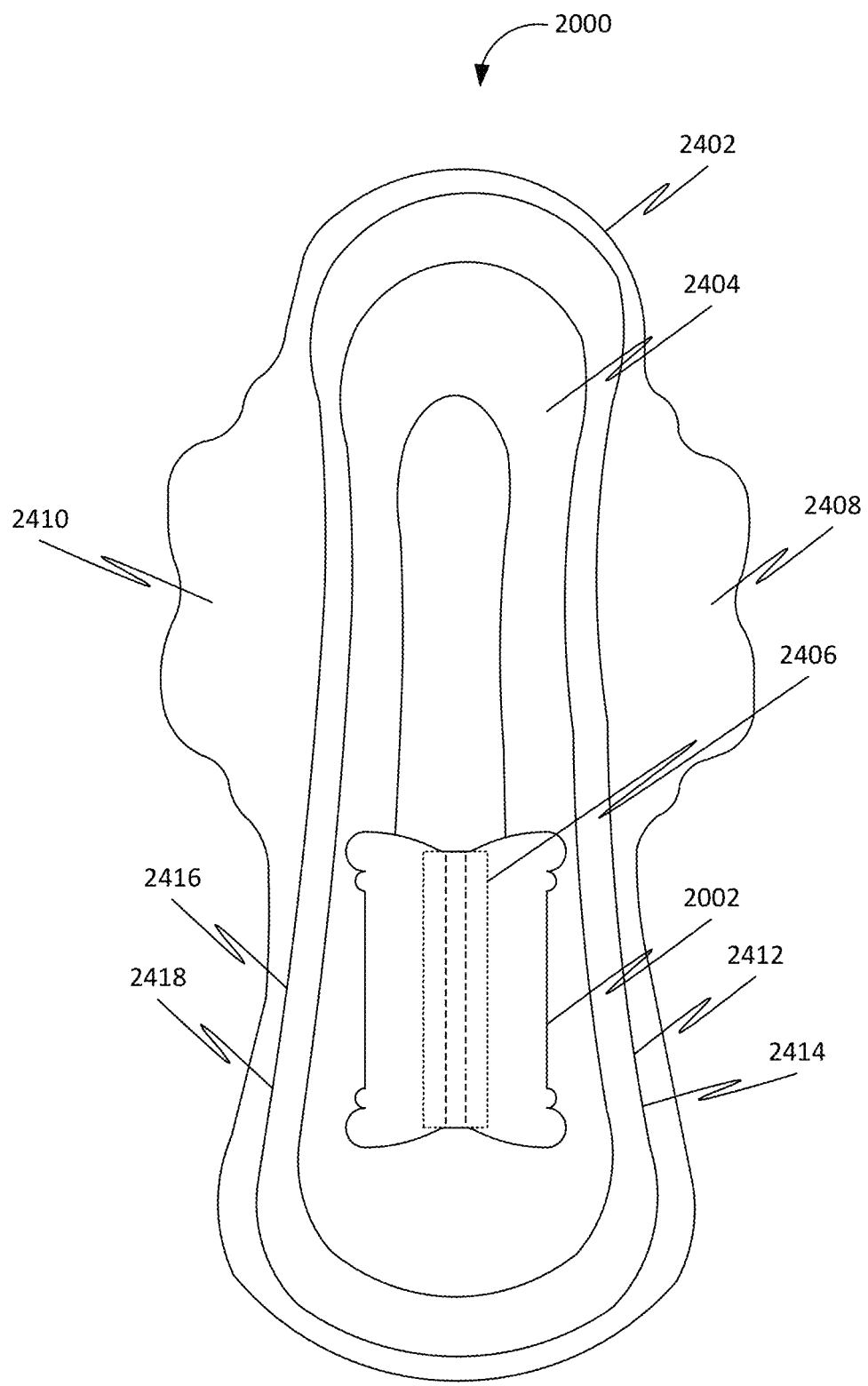
FIG. 24 is a top view of the article 2000 with the absorbent element 2002 attached to the absorbent pad 2402, in accordance with some embodiments.

Further, in some embodiments, the absorbent element 2002 may be configured to be attached to a surface portion 2406 of a top surface 2404 of an absorbent pad 2402, as shown in FIG. 24. Further, the absorbent element 2002 may be centrally and longitudinally attached to the absorbent pad 2402 based on the attaching of the absorbent element 2002 to the surface portion 2406 of the top surface 2404 of the absorbent pad 2402. Further, the surface portion 2406 of the top surface 2404 may be marked with at least one marking. Further, the at least one marking indicates a stick-to place on the absorbent pad 2402. Further, the at least one marking may include a color. Further, in an embodiment, the absorbent pad 2402 may be associated with a plurality of sizes. Further, the plurality of sizes may include three sizes.

Further, in an embodiment, the absorbent pad 2402 may include a first wing portion 2408 and a second wing portion 2410. Further, the first wing portion 2408 may extend from a first side 2412 of the absorbent pad 2402 along at least a portion of a periphery 2414 of the absorbent pad 2402 corresponding to the first side 2412 and the second wing portion 2410 may extend from a second side 2416 of the absorbent pad 2402 along at least a portion of a periphery 2418 of the absorbent pad 2402 corresponding to the second side 2416. Further, the first side 2412 opposes the second side 2416.

Further, in an embodiment, at least one of the first wing portion 2408 and the second wing portion 2410 may include at least one branding.

Further, in some embodiments, the absorbent element 2002 may be associated with a plurality of sizes. Further, the plurality of sizes may include a first size, a second size, and a third size. Further, the absorbent element 2002 of the first size has a width of 57.5 mm and a length of 80 mm. Further, the absorbent element 2002 of the second size has a width of 67.5 mm and a length of 90 mm. Further, the absorbent element 2002 of the third size has a width of 87.5 mm and a length of 110 mm.

Figure 21:
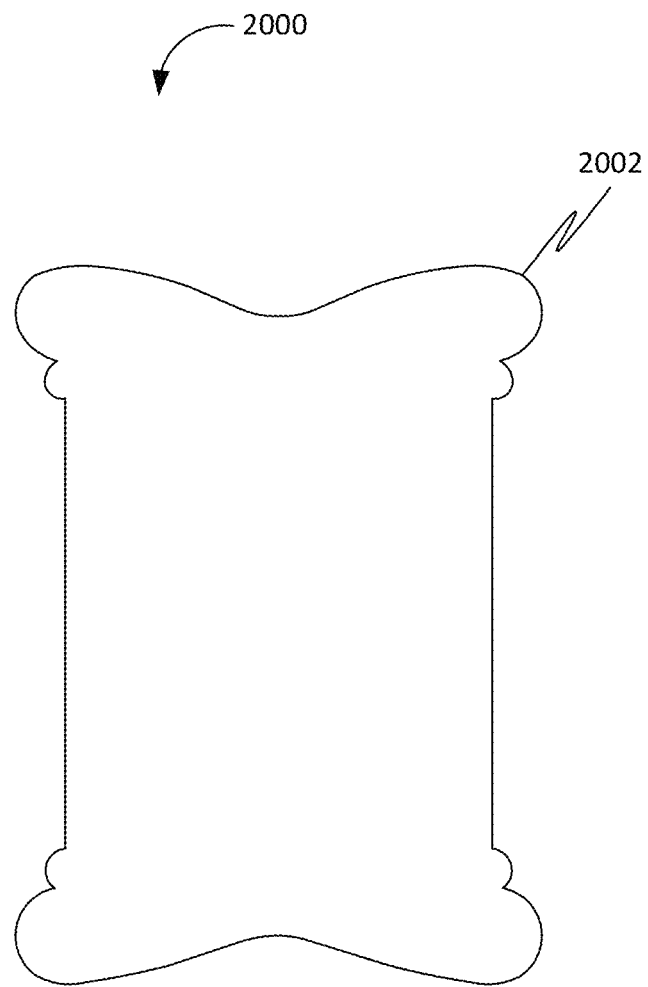
FIG. 21 is a bottom view of the article 2000, in accordance with some embodiments.

FIG. 21 is a bottom view of the article 2000, in accordance with some embodiments.

FIG. 22 is a top perspective view of the article 2000 comprising the backsheet 2202 with the absorbent element 2002, in accordance with some embodiments.

FIG. 23 is a top view of the article 2000, in accordance with some embodiments.

FIG. 24 is a top view of the article 2000 with the absorbent element 2002 attached to the absorbent pad 2402, in accordance with some embodiments.

Figure 25:
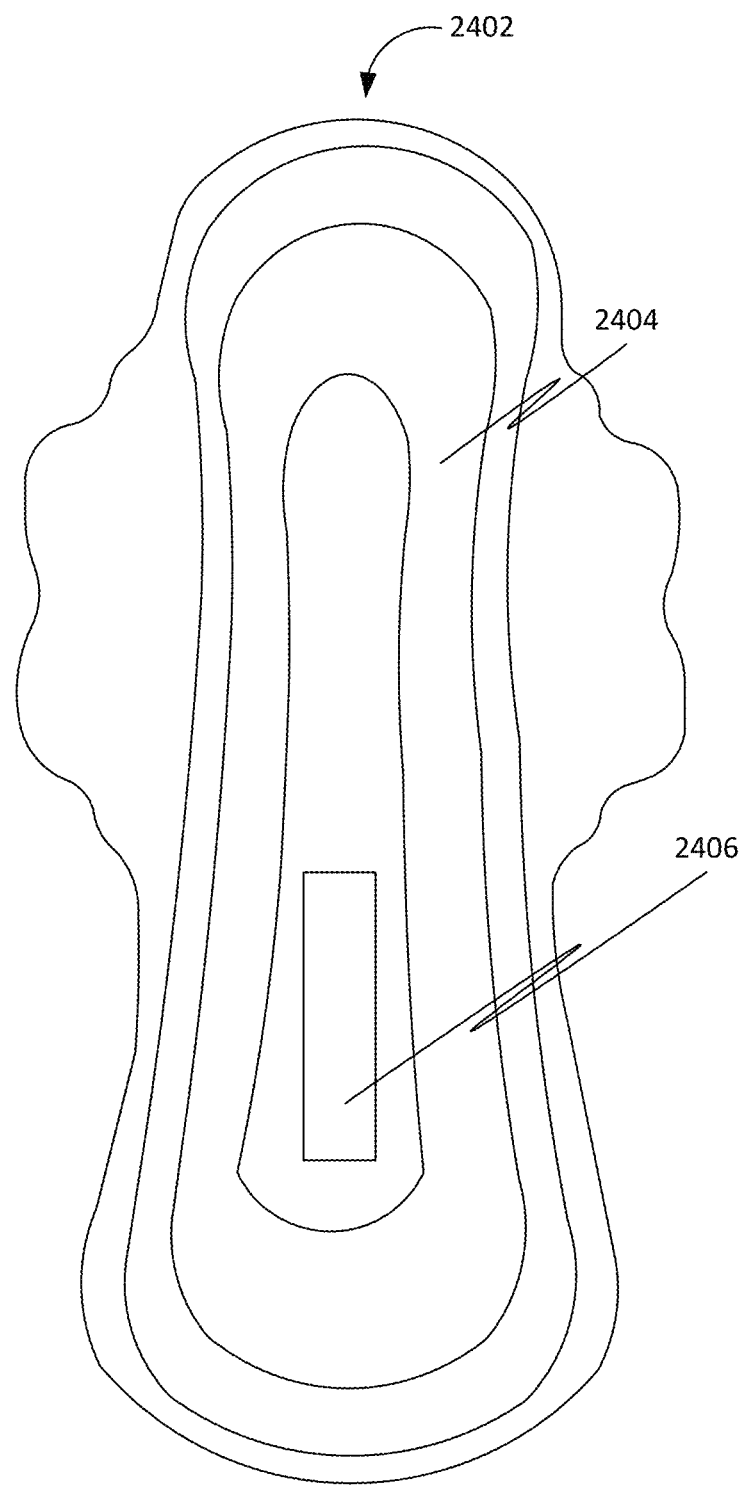
FIG. 25 is a top view of the absorbent pad 2402, in accordance with some embodiments.

FIG. 25 is a top view of the absorbent pad 2402, in accordance with some embodiments.

Although the present disclosure has been explained in relation to its preferred embodiment, it is to be understood that many other possible modifications and variations can be made without departing from the spirit and scope of the disclosure.

What is claimed is:

1. An article for absorbing bodily discharges of a user, the article comprising:
an absorbent element configured to be disposed in an intergluteal cleft of the user, wherein the absorbent element comprises a base portion, a first portion, and a second portion, wherein the first portion is attached to the base portion on a first side of the base portion and the second portion is attached to the base portion on a second side of the base portion, wherein the first side opposes the second side, wherein each of the first portion and the second portion extends vertically away from the base portion, wherein the absorbent element comprises an outer layer and an inner layer, wherein the inner layer is disposed below the outer layer, wherein the outer layer collects a bodily discharge of the user and the inner layer absorbs the bodily discharge collected by the outer layer, wherein the first portion corresponds to a right gluteal region of the user and the second portion corresponds to a left gluteal region of the user, wherein each of the first portion and the second portion comprises an attaching element disposed on a periphery of each of the first portion and the second portion, wherein the attaching element of the first portion is configured to secure the first portion on at least a portion of the right gluteal region, wherein the attaching element of the second portion is configured to secure the second portion on at least a portion of the left gluteal region, wherein each of the first portion and the second portion comprises a first end and a second end, the first portion and the second portion longitudinally extend beyond the base portion at the first end, and the first portion and the second portion longitudinally extend beyond the base portion at the second end.

2. The article of claim 1 further comprising an absorbent pad configured to be disposed in at least a portion of a crotch region of the user, wherein the absorbent pad comprises a top layer, a bottom layer, and at least one absorbent material layer, wherein the top layer opposes at least the portion of the crotch region based on the disposing of the absorbent pad in at least the portion of the crotch region, wherein the bottom layer is disposed below the top layer, wherein the at least one absorbent material layer is disposed between the top layer and the bottom layer, wherein the absorbent element is attached to the absorbent pad, wherein the disposing of the absorbent element in the intergluteal cleft is based on the disposing of the absorbent pad in at least the portion of the crotch region of the user.

3. The article of claim 2, wherein the base portion comprises at least one attaching element disposed on a bottom side of the base portion, wherein the absorbent element is attached to the absorbent pad based on the at least one attaching element.

4. The article of claim 2, wherein the absorbent pad comprises a front portion and a rear portion, wherein the absorbent element is further attached to the rear portion of the absorbent pad.

5. The article of claim 4, wherein the absorbent element is further centrally and longitudinally attached to the rear portion of the absorbent pad.

6. The article of claim 1, wherein each of the first portion and the second portion comprises an outer surface and an inner surface, wherein the outer surface of the first portion is configured to face the right gluteal region and the outer surface of the second portion is configured to face the left gluteal region based on the disposing of the absorbent element in the intergluteal cleft of the user.

7. The article of claim 1, wherein the first portion and the second portion define a space between the first portion and the second portion based on the attaching of the first portion to the first side of the base portion and the attaching of the second portion to the second side of the base portion.

8. The article of claim 1, wherein the first portion is flexibly attached to the first side of the base portion defining a first line of attachment and the second portion is flexibly attached to the second side of the base portion defining a second line of attachment, wherein each of the first portion and the second portion is configured to move between a plurality of positions about each of the first line of attachment and the second line of attachment based on the flexibly attaching of the first portion to the first side of the base portion and the second portion to the second side of the base portion.

9. The article of claim 1, wherein each of the first portion and the second portion is characterized by a length and a width, wherein each of the first portion and the second portion extends between the first end and the second end, wherein the width of at least one of the first portion and the second portion progressively decreases from the second end of at least one of the first portion and the second portion to the first end of at least one of the first portion and the second portion along the length of at least one of the first portion and the second portion.

10. The article of claim 1, wherein each of the first portion and the second portion is characterized by a length and a thickness, wherein each of the first portion and the second portion extends between the first end and the second end, wherein the thickness of at least one of the first portion and the second portion progressively decreases from the second end of at least one of the first portion and the second portion to the first end of at least one of the first portion and the second portion along the length of at least one of the first portion and the second portion.

11. An article for absorbing bodily discharges of a user, the article comprising:

an absorbent element configured to be disposed in an intergluteal cleft of the user, wherein the absorbent element comprises a base portion, a first portion, and a second portion, wherein the first portion is attached to the base portion on a first side of the base portion and the second portion is attached to the base portion on a second side of the base portion, wherein the first side opposes the second side, wherein each of the first portion and the second portion extends vertically away from the base portion, wherein the absorbent element comprises an outer layer and an inner layer, wherein the inner layer is disposed below the outer layer, wherein the outer layer collects a bodily discharge of the user and the inner layer absorbs the bodily discharge collected by the outer layer, wherein the first portion corresponds to a right gluteal region of the user and the second portion corresponds to a left gluteal region of the user, wherein each of the first portion and the second portion comprises an attaching element disposed on a periphery of each of the first portion and the second portion, wherein the attaching element of the first portion is configured to secure the first portion on at least a portion of the right gluteal region, wherein the attaching element of the second portion is configured to secure the second portion on at least a portion of the left gluteal region, wherein each of the first portion and the second portion comprises a first end and a second end, the first portion and the second portion longitudinally extend beyond the base portion at the first end, and the first portion and the second portion longitudinally extend beyond the base portion at the second end; and an absorbent pad configured to be disposed in at least a portion of a crotch region of the user, wherein the absorbent pad comprises a top layer, a bottom layer, and at least one absorbent material layer, wherein the top layer opposes at least the portion of the crotch region based on the disposing of the absorbent pad in at least the portion of the crotch region, wherein the bottom layer is disposed below the top layer, wherein the at least one absorbent material layer is disposed between the top layer and the bottom layer, wherein the absorbent element is attached to the absorbent pad, wherein the disposing of the absorbent element in the intergluteal cleft is based on the disposing of the absorbent pad in at least the portion of the crotch region of the user.

12. The article of claim 11, wherein the base portion comprises at least one attaching element disposed on a bottom side of the base portion, wherein the absorbent element is attached to the absorbent pad based on the at least one attaching element.

13. The article of claim 11, wherein the absorbent pad comprises a front portion and a rear portion, wherein the absorbent element is further attached to the rear portion of the absorbent pad.

14. The article of claim 11, wherein each of the first portion and the second portion comprises an outer surface and an inner surface, wherein the outer surface of the first portion is configured to face the right gluteal region and the outer surface of the second portion is configured to face the left gluteal region based on the disposing of the absorbent element in the intergluteal cleft of the user.

15. The article of claim 11, wherein the first portion and the second portion define a space between the first portion and the second portion based on the attaching of the first portion to the first side of the base portion and the attaching of the second portion to the second side of the base portion.

16. The article of claim 11, wherein the first portion is flexibly attached to the first side of the base portion defining a first line of attachment and the second portion is flexibly attached to the second side of the base portion defining a second line of attachment, wherein each of the first portion and the second portion is configured to move between a plurality of positions about each of the first line of attachment and the second line of attachment based on the flexibly attaching of the first portion to the first side of the base portion and the second portion to the second side of the base portion.

17. The article of claim 11, wherein each of the first portion and the second portion is characterized by a length and a width, wherein each of the first portion and the second portion extends between the first end and the second end, wherein the width of at least one of the first portion and the second portion progressively decreases from the second end of at least one of the first portion and the second portion to the first end of at least one of the first portion and the second portion along the length of at least one of the first portion and the second portion.

18. An article for absorbing bodily discharges of a user, the article comprising:
an absorbent element configured to be disposed in an intergluteal cleft of the user, wherein the absorbent element comprises a base portion, a first portion, and a second portion, wherein the first portion is attached to the base portion on a first side of the base portion and the second portion is attached to the base portion on a second side of the base portion, wherein the first side opposes the second side, wherein each of the first portion and the second portion extends vertically away from the base portion, wherein the absorbent element comprises an outer layer and an inner layer, wherein the inner layer is disposed below the outer layer, wherein the outer layer collects a bodily discharge of the user and the inner layer absorbs the bodily discharge collected by the outer layer, wherein the first portion corresponds to a right gluteal region of the user and the second portion corresponds to a left gluteal region of the user, wherein each of the first portion and the second portion comprises an attaching element disposed on a periphery of each of the first portion and the second portion, wherein the attaching element of the first portion is configured to secure the first portion on at least a portion of the right gluteal region, wherein the attaching element of the second portion is configured to secure the second portion on at least a portion of the left gluteal region, wherein each of the first portion and the second portion comprises a first end and a second end, the first portion and the second portion longitudinally extend beyond the base portion at the first end, and the first portion and the second portion longitudinally extend beyond the base portion at the second end; and an absorbent pad configured to be disposed in at least a portion of a crotch region of the user, wherein the absorbent pad comprises a top layer, a bottom layer, and at least one absorbent material layer, wherein the top layer opposes at least the portion of the crotch region based on the disposing of the absorbent pad in at least the portion of the crotch region, wherein the bottom layer is disposed below the top layer, wherein the at least one absorbent material layer is disposed between the top layer and the bottom layer, wherein the absorbent element is attached to the absorbent pad, wherein the disposing of the absorbent element in the intergluteal cleft is based on the disposing of the absorbent pad in at least the portion of the crotch region of the user, wherein the absorbent pad comprises a front portion and a rear portion, wherein the absorbent element is further attached to the rear portion of the absorbent pad, wherein the absorbent element is further centrally and longitudinally attached to the rear portion of the absorbent pad.

19. The article of claim 18, wherein the base portion comprises at least one attaching element disposed on a bottom side of the base portion, wherein the absorbent element is attached to the absorbent pad based on the at least one attaching element.

\* \* \* \* \*